(12) United States Patent
Cadle-Davidson et al.

(10) Patent No.: US 12,096,775 B2
(45) Date of Patent: Sep. 24, 2024

(54) METHOD OF STABLE FORMULATION OF MICROBIAL AND MICROBE DERIVED PRODUCTS AND USE OF SAME

(71) Applicant: ADVANCED BIOLOGICAL MARKETING, INC., Geneva, NY (US)

(72) Inventors: Molly Cadle-Davidson, Geneva, NY (US); Robert Patrick, Waterloo, NY (US); Brenden Otero, Newark, NY (US); Rebecca Cheng, Canandaigua, NY (US)

(73) Assignee: Advanced Biological Marketing, Inc., Geneva, NY (US)

( * ) Notice: Subject to any disclaimer, the term of this patent is extended or adjusted under 35 U.S.C. 154(b) by 112 days.

(21) Appl. No.: 17/233,493

(22) Filed: Apr. 18, 2021

(65) Prior Publication Data

US 2021/0321625 A1     Oct. 21, 2021

Related U.S. Application Data

(60) Provisional application No. 63/011,367, filed on Apr. 17, 2020.

(51) Int. Cl.
*A01N 63/38*     (2020.01)
*A01N 25/04*     (2006.01)
*A01N 25/22*     (2006.01)

(52) U.S. Cl.
CPC ............. *A01N 63/38* (2020.01); *A01N 25/04* (2013.01); *A01N 25/22* (2013.01)

(58) Field of Classification Search
CPC ........ A01N 63/38; A01N 25/04; A01N 25/22; A01P 1/00; C12R 2001/885; A61K 47/10; A61K 47/24; A61K 47/36; A61K 47/44; A61K 9/10
See application file for complete search history.

(56) References Cited

U.S. PATENT DOCUMENTS

| | | | |
|---|---|---|---|
| 2012/0058225 A1 | 3/2012 | Kirejevas et al. | |
| 2016/0015029 A1* | 1/2016 | Baseeth | A61K 36/48 514/783 |
| 2020/0085065 A1 | 3/2020 | Kellar et al. | |

FOREIGN PATENT DOCUMENTS

| | | | | |
|---|---|---|---|---|
| CN | 105707897 A | 6/2016 | | |
| CN | 107582573 A | 1/2018 | | |
| WO | WO-2018183978 A1 * | 10/2018 | ............... | A01C 1/06 |
| WO | WO-2018218035 A1 * | 11/2018 | ............... | A01N 63/00 |
| WO | WO-2018232201 A1 * | 12/2018 | ............... | B22D 1/005 |
| WO | WO-2021022128 A1 * | 2/2021 | ............... | A01N 25/22 |

OTHER PUBLICATIONS

Agripino de Medeiros et al., Tomato progeny inherit resistance to the nematode Meloidogyne javanica linked to plant growth induced by the biocontrol fungus, Scientific Reports, 7, 40216 published Jan. 10, 2017 (Year: 2017).*
International Search Report and Written Opinion for International Application No. PCT/US2021/027961 dated Aug. 3, 2021 (24 pages).
International Preliminary Report on Patentability for PCT/US2021/027961 dated Oct. 27, 2022, (7 pages).

* cited by examiner

*Primary Examiner* — Nicole P Babson
*Assistant Examiner* — Edwin Coleman Mitchell
(74) *Attorney, Agent, or Firm* — Reising Ethington P.C.

(57) ABSTRACT

Disclosed are shelf stable water miscible suspension systems for suspending microbes and/or microbe derived metabolites so they are water dispersible and can be combined with a variety of agricultural chemicals in an aqueous solution. The microbes and/or microbe derived metabolites are initially suspended in a plant derived oil and then this oil suspension is converted to a water dispersible suspension using one of the disclosed suspension systems. The microbe and/or microbe derived metabolites in the suspension systems are shelf stable for at least 52 weeks at 25° C.

31 Claims, 20 Drawing Sheets

METHOD OF STABLE FORMULATION OF MICROBIAL AND MICROBE DERIVED PRODUCTS AND USE OF SAME

CROSS-REFERENCE TO RELATED APPLICATIONS

This application claims the benefit of U.S. Provisional Application No. 63/011,367, filed on Apr. 17, 2020.

STATEMENT REGARDING FEDERALLY SPONSORED RESEARCH

NONE.

STATEMENT REGARDING JOINT DEVELOPMENT AGREEMENT

NONE.

REFERENCE TO SEQUENCING LISTING, TABLE OR COMPUTER PROGRAM LISTING

NONE.

STATEMENT REGARDING PRIOR DISCLOSURES BY THE INVENTOR OR A JOINT INVENTOR UNDER 33 C.F.R 1.77(B)(6)

NONE.

FIELD OF THE DISCLOSURE

This present disclosure relates generally to use of microbes and/or microbial derived metabolites in combination with agricultural chemicals, and more particularly to a shelf stable and water dispersible formulations of agriculturally relevant microbes and/or microbial derived metabolites in combination with agricultural chemicals.

BACKGROUND OF THE DISCLOSURE

This section provides background information which is not necessarily prior art to the inventive concepts associated with the present disclosure.

Microbial agricultural products are frequently used in combination with conventional agricultural chemistries, however the two types of products have dramatically different characteristics. Chemistries are often suspensions, mixtures, colloids, or other types of aggregates that combine reactive chemicals in such a way as to achieve their stability for a required two year minimum. The individual components of these mixtures can range from simple salts, to lipids and surfactants, to complex or activated polymers. In contrast, microbial products consist of living cellular organisms and/or their byproducts, many aspects of which are vulnerable to disruption by the components of agricultural chemistry solutions. The trend in the marketplace to use these two types of components in the same system requires that they are compatible on several levels. One compatibility is at the chemical level. A second compatibility is shelf life, or formulation stability. Since chemistries are required to be stable for two years on the shelf before use, it is desirable that microbial products maintain that same stability in order that suppliers are not limited by the restrictions of that component. At this time, there is no regulatory requirement for microbial products to maintain any particular shelf life and products in the 2020 marketplace are highly variable in their shelf life claims and support for those claims. The current invention address both the chemical compatibility and shelf life of microbial products by describing liquid shelf stable and water dispersible formulations with more than 12 months of shelf stability and excellent compatibility with a wide range of current agricultural chemistries and aqueous formulations.

The main issue with existing technologies is that the microbes and microbial metabolites are not room temperature shelf stable especially when in liquid formulations with the relevant agricultural chemicals. This is particularly evident when the liquid formulation is an aqueous liquid. Dry fungal or bacterial spores are exceptionally stable structures; however, when hydrated they begin to take up water and initiate germination. This leads to rapid cell death if the solution osmotic conditions, nutrient composition, or pH are unsuitable for continued growth or if toxins are present. Even if refrigerated the shelf life stability is not acceptable. Thus, often the microbes or their metabolites have to be stored under refrigeration or frozen and then combined with the other agricultural chemicals shortly before use. The lack of shelf stability of the microbes is measured by their decrease in colony forming units (cfu) per milliliter of microbial composition. Once applied to the seeds, soil, foliage or harvested product the microbial products retain excellent activity; however, liquid microbial formulations generally lose cfu viability while in their commercial packaging, long before the other agricultural chemicals they are combined with lose their chemical potency.

It is desirable to provide a method and system for combining microbes and/or their metabolites in a formulation that is shelf stable for at least 12 months or longer at room temperature, water dispersible and that is compatible with typical agricultural chemicals as described herein.

SUMMARY OF THE DISCLOSURE

This section provides a general summary of the present disclosure and is not intended to be interpreted as a comprehensive disclosure of its full scope or all features, aspects and objectives.

One aspect of the present disclosure is to provide a suspension system for forming shelf stable microbes and/or microbial metabolites comprising: an oil suspension of at least one microbe in a plant derived oil combined with; an aqueous solution or a non-aqueous solution comprising at least one galactomannan polysaccharide emulsifier; optionally, an amphiphilic glycerophospholipid emulsion stabilizer; and a dispersing agent. The combination of the oil suspension with either the aqueous or non-aqueous galactomannan polysaccharide containing solution can be done at the time of use or at least up to one year prior to the time of use under the proper storage conditions as described herein. The suspension systems are water dispersible and fully miscible with aqueous solutions.

Another aspect of the present disclosure is to provide a suspension system for forming a shelf stable, water dispersible, suspension of microbes and/or microbial metabolites comprising an emulsion of water, an oil suspension of the microbes and/or microbial metabolites and, optionally at least one of a cyclodextrin(s), organic material, such as humic acids (CAS 1415-93-6), galactomannan polysaccharide emulsifier, at least one preservative as described herein, a yeast extract such as CAS 8013-01-2, glycerol, a nitrogen source such as urea, and mixtures thereof.

Another aspect of the present disclosure is to provide a suspension system for forming a shelf stable, water miscible, suspension of microbes and/or microbial metabolites comprising an emulsion of glycerol, an oil suspension of the microbes and/or microbial metabolites, a dispersing agent, and, optionally, at least one galactomannan polysaccharide emulsifier.

These and other features and advantages of this disclosure will become more apparent to those skilled in the art from the detailed description herein. The drawings that accompany the detailed description are described below.

BRIEF DESCRIPTION OF THE DRAWINGS

The drawings described herein are for illustrative purposes only of selected aspects and not all implementations, and are not intended to limit the present disclosure to only that actually shown. With this in mind, various features and advantages of example aspects of the present disclosure will become apparent to one possessing ordinary skill in the art from the following written description and appended claims when considered in combination with the appended drawings, in which:

FIG. 10 is a photograph showing a tank mix of suspension system 2 according to the present disclosure;

DETAILED DESCRIPTION OF THE DISCLOSURE

Figure 1A:
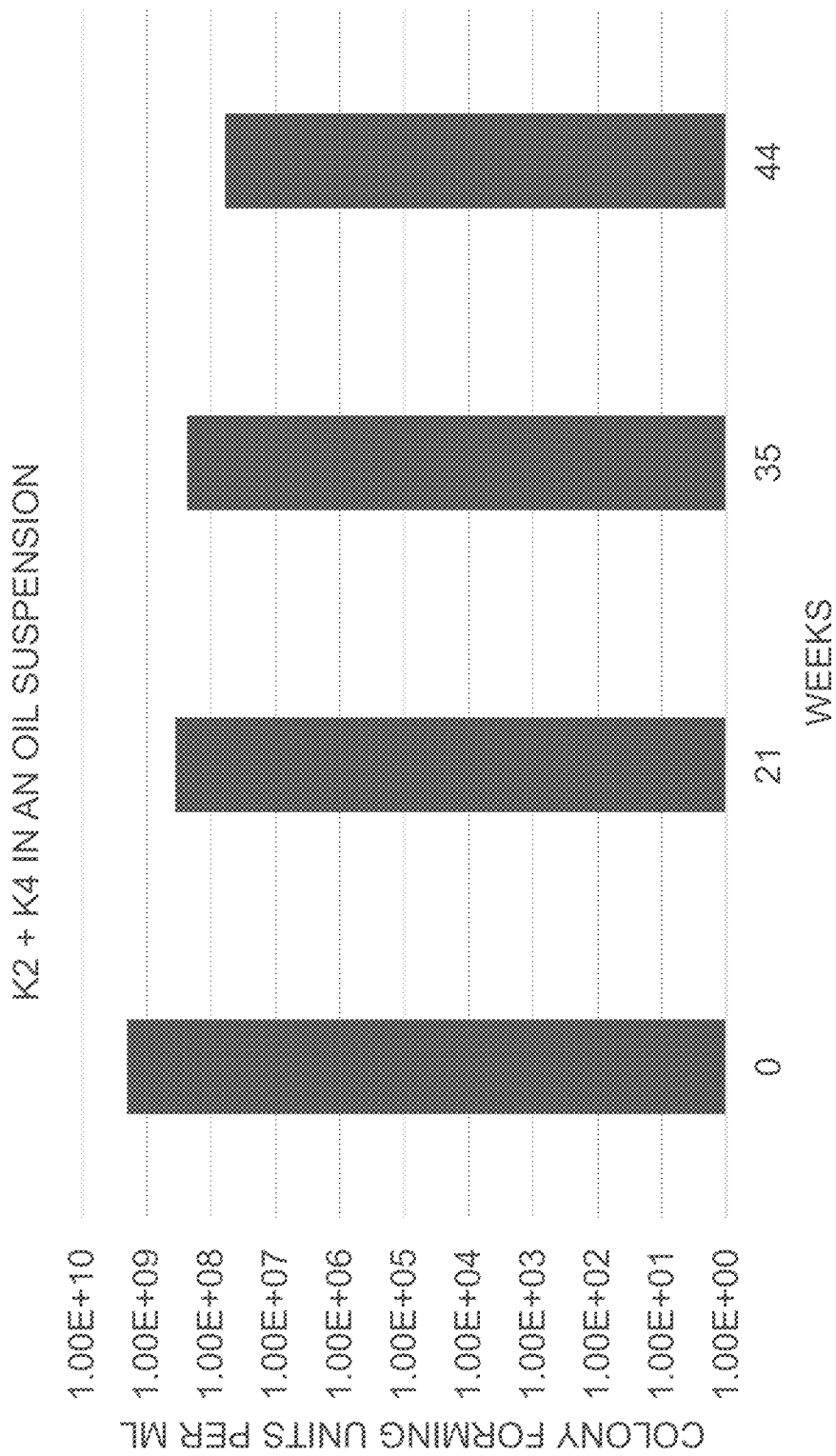
FIG. 1A is a graph showing the shelf stability over time of an oil suspension according to the present invention of a combination of the microbes *Trichoderma afroharzianum*, strain K2, and *Trichoderma atroviride*, strain K4, stored at a temperature of from 22 to 25° C.

In the following description, details are set forth to provide an understanding of the present disclosure.

For clarity purposes, example aspects are discussed herein to convey the scope of the disclosure to those skilled in the relevant art. Numerous specific details are set forth such as examples of specific components, devices, and methods, in order to provide a thorough understanding of various aspects of the present disclosure. It will be apparent to those skilled in the art that specific details need not be discussed herein, such as well-known processes, well-known device structures, and well-known technologies, as they are already well understood by those skilled in the art, and that example embodiments may be embodied in many different forms and that neither should be construed to limit the scope of the disclosure.

The terminology used herein is for the purpose of describing particular example aspects only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or feature is referred to as being "on," "engaged to," "connected to," "coupled to" "operably connected to" or "in operable communication with" another element or feature, it may be directly on, engaged, connected or coupled to the other element or layer, or intervening elements or features may be present. In contrast, when an element is referred to as being "directly on," "directly engaged to," "directly connected to," or "directly coupled to" another element or feature, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly and expressly indicated by the context. Thus, a first element, component, region, layer or section discussed below could be termed a second element, component, region, layer or section without departing from the teachings of the example embodiments.

For purposes of description herein, the terms "upper," "lower," "right," "left," "rear," "front," "vertical," "horizontal," and derivatives thereof shall relate to the invention as oriented in the FIGS. However, it is to be understood that the present disclosure may assume various alternative orientations and step sequences, except where expressly specified to the contrary. It is also to be understood that the specific devices and processes illustrated in the attached drawings, and described in the following specification are exemplary aspects of the inventive concepts defined in the appended claims. Hence, specific dimensions and other physical characteristics relating to the aspects disclosed herein are not to be considered as limiting, unless the claims expressly state otherwise.

In the present specification and claims the term "shelf stable" means that the formulation maintains a colony forming unit (cfu) measure of at least $10^8$ colony forming units per milliliter (cfu/ml) of formulation or greater over the indicated time at the indicated temperature, for the present disclosure preferably this means shelf stability of at least 52 weeks at a temperature of 22 to 25° C., although shorter time periods apply to some embodiments. The term "water dispersible" means the formulation or suspension system is fully miscible in an aqueous solution. All ranges for components provided herein include all subranges inclusively between the specifically described ranges.

The present invention relates generally to formulations entailing one or more microbes and/or one or more microbial derived metabolites in a water dispersible suspension that exhibits shelf stability. Secondarily, the present invention is directed to use of these shelf stable and water dispersible formulations in combination with other agricultural chemicals in aqueous solutions. The relevant agricultural chemicals include, by way of example: a fungicide, an insecticide, a nematicide, a bactericide, an herbicide, pesticide, a fertilizer, a surfactant, an adjuvant, or any combination of these agricultural chemicals. Generally, these agricultural chemicals are either already aqueous solutions or they are diluted into aqueous solutions prior to use. These relevant agricultural chemicals tend to be fully miscible in aqueous solutions.

The microbes of particular interest according to the present invention are dry fungal spores of the following species: *Trichoderma virens*; *Trichoderma atroviride*; *Trichoderma afroharzianum*; *Trichoderma* K1 a strain of *Trichoderma virens* with an ATCC number of 20906 disclosed in at least U.S. Pat. No. 5,165,928; *Trichoderma* K2 a strain of *Trichoderma afroharzianum* with an ATCC number of PTA-9708 disclosed in U.S. Pat. No. 8,716,001; *Trichoderma* K3 a strain of *Trichoderma afroharzianum* with an ATCC number of PTA-9709 disclosed in U.S. Pat. No. 8,877,481; *Trichoderma* K4 a strain of *Trichoderma atroviride* with an ATCC number of PTA-9707 disclosed in U.S. Pat. No. 8,877,480; *Trichoderma* K5 a strain of *Trichoderma atroviride* with an NRRL number of 50520 and disclosed in PCT application number PCT/US2012/066329 filed on Nov. 21, 2012 and published on May 30, 2013 as WO/2013/078365; and mixtures of these species. The microbial metabolites from these species of particular interest are: 6-pentyl-pyrone; harzianic acid; the hydrophobic protein HYTRA 1; harzinolide; 1-octene-3-ol; and mixtures of these metabolites. The *Trichoderma* K1, a strain of *Trichoderma virens* with an ATCC number of 20906, can easily be cultured by purchasing liquid SabrEx® for soybeans from Advanced Biological Marketing and culturing it on potato dextrose agar in the presence of Igepal® CA-630 as described herein.

The present invention provides water dispersible formulations of these microbes and/or microbial metabolites wherein the water dispersible formulations are shelf stable, meaning they retain high levels of colony forming units (cfu) over an extended period of time at room temperatures of approximately 25° C. for 12 months or more. The formulations are shelf stable for several years when stored at refrigerated temperatures of 5° C. or less. The formulations can be diluted with aqueous solutions as required during application and are compatible with all manner of application equipment and other agricultural chemicals. The formulations can be applied onto the seeds, in the furrow, by soil drench, by root dip, by foliar spray, by side dress, or by other means to a crop.

The first step in creating the suspension systems according to the present invention is to suspend the microbes, typically dry fungal spores, and, optionally, their metabolites as defined above, in a plant derived oil at a level of at least $10^8$ cfu/ml, preferably higher to create an oil suspension. The oil suspensions containing the microbial metabolites preferably have the metabolites present in an amount of from 0.40 to 5.0% by weight based on the total weight of the oil suspension. The plant derived oils finding use in the present invention include all plant derived oils, including by way of example: soybean oil; canola oil; corn oil; peanut oil; rapeseed oil; sunflower oil; cottonseed oil; palm oil; coconut oil; safflower oil, sesame oil, and mixtures of two or more of these oils. While the oil suspension of the microbes shows very significant long term viability as shown in the prior art, these oil suspensions are not miscible in aqueous solutions. Virtually all the other agricultural chemicals, as disclosed above, are miscible in aqueous solutions and during application they are diluted into aqueous solutions. Preferably, the oil suspensions according to the present disclosure consist essentially of one or more plant derived oils and at least one microbe or more, or at least one microbial metabolite or more, or of a mixture of one or more microbes and one or more microbial metabolites.

The second step in the process is to incorporate the oil suspension of microbes and/or their metabolites into a water dispersible solution using one of the at least three suspension systems as described herein. In a first suspension system the oil suspension prepared as above, is diluted into a non-aqueous solution comprising: at least one galactomannan polysaccharide emulsifier; optionally, an amphiphilic glycerophospholipid emulsion stabilizer; and a dispersing agent. This process provides a water dispersible formulation that is shelf stable for more than 12 months at room temperature of approximately 25° C., is unaffected by freezing, fully miscible in aqueous solutions and is shelf stable at 40° C. for 4 weeks. As is known to those of skill in the art, testing shelf stability at 40° C. is a recognized standard of the Collaborative International Pesticides Analytical Council (CIPAC). Under their standards 8 weeks at 40° C. is representative of 2 years storage at room temperature of 25° C. Generally, the standard is applied to chemical stability testing rather than microbial viability. In the present specification and claims when a suspension system is referred to as suspension system 1, it means this suspension system. The preferred ranges of the components of this suspension system 1 are shown below in TABLE 1. The wgt % is based on the total formulation weight and the cfu/ml level of each microbe in the final water miscible formulation must be at least $10^8$ cfu/ml, however it can exceed this level as desired. The suspension system, suspension system 1, as shown in TABLE 1 requires no other components to provide a shelf stable formulation and can be formulated to consist essentially of an oil suspension as described, at least one galactomannan polysaccharide, a dispersing agent and, optionally, an amphiphilic glycerophospholipid.

TABLE 1

| COMPONENT | FINAL FORMULATION AMOUNT |
|---|---|
| Oil suspension of microbes and/or microbial metabolites | 70 to 97.5 wgt % of oil suspension providing in the final formulation $10^8$ cfu/ml or more, 0.28 to 4.9 wgt % of a metabolite |
| Galactomannan polysaccharide | 2 to 17.5 wgt % |
| Amphiphilic Glycerophospholipid | 0 to 1.0 wgt % |
| Dispersing agent | 0.5 to 17.5 wgt % |

In an alternative embodiment, the oil suspension can be combined with an aqueous solution comprising at least one galactomannan polysaccharide emulsifier, glycerol, and a preservative. In this embodiment, the system can be provided as a two component kit of suspension system 1 to leverage the long shelf stability of the oil suspension of the at least one of a microbe, a microbe derived metabolite or a combination thereof. The kit also utilizes the emulsification and water dispersion properties of the galactomannan polysaccharide. In this kit, the oil suspension provides one component and an aqueous suspension of the other ingredients provides the other component. The component one comprises: 80 to 99.6 wgt % of the oil along with 0.4 to 5 wgt % of the microbe derived metabolite, or 2 to 20 wgt % of at least one microbe this amount being sufficient to provide at least $10^8$ CFU/ml in the final combined formulation, or a combination of at least one microbe and at least one microbe derived metabolite, the total being 100 wgt %. The component two comprises: 0.3 to 10 wgt % of the one or more galactomannan polysaccharide emulsifiers; 10 to 30 wgt % of glycerol; 0.1 to 2 wgt % of a preservative, such as sodium propionate, or 1,2 benzisothiazol-3(2-H)-1, or others known to those of skill in the art; and 60 to 90 wgt % of reverse osmosis water, to make 100 wgt %. The component one and component two can be combined together to form the water miscible suspension up to 6 months in advance of use. The component one and component two can be combined in volume:volume ratios of from 1:4 to 4:1, the two component kit would include instructions regrading this mixing ratio and the process of mixing.

The formulation according to Table 1 includes the use of a galactomannan polysaccharide as an emulsifier. As is known in the art the galactomannan polysaccharides have a backbone of 1-4 linked beta-D-mannopyranose with the galactose side groups branching from the 6 position of the mannopyranose as a 1-6 linked alpha-D-galactopyranose unit. There are many examples of galactomannan polysaccharides including, by way of example: fenugreek gum, which has a ratio of mannose to galactose units of 1:1; guar gum, which has a ratio of mannose to galactose units of 2:1; tara gum, which has a ratio of mannose to galactose units of 3:1; locust bean gum, which has a ratio of mannose to galactose units of 4:1; and cassia gum, which has a ratio of mannose to galactose units of 5:1. In the present disclosure, the suspension system can comprise anyone of the galactomannan polysaccharides either alone or in any combination of galactomannan polysaccharides.

The amphiphilic glycerophospholipid, which is optional, serves as an emulsion stabilizer. As is known in the art the glycerophospholipids are the main components of biological membranes and they have three main parts. A glycerol backbone having ester linkages with two, nonpolar fatty acid lipid groups and a polar phosphate ester group. The fatty acid portion comprises the hydrophobic part and the phosphate ester group is hydrophilic. The main classes of glycerophospholipids are plasmalogens and phosphatidates. In the phosphatidates the structure comprises the two fatty acids and the phosphate is linked to an alcohol like ethanolamine, a choline, a serine or a carbohydrate. Lecithin is a common example of a mixture of glycerophospholipids and finds special use as the emulsion stabilizer in the present invention. Lecithins are mixtures of glycerophospholipids including phosphatidylcholine, phosphatidylethanolamine, phosphatidylinositol, phosphatidylserine, and phosphatidic acid.

The dispersing agents finding use in the present invention include organic and inorganic compounds. One such example is siloxane polyalkyleneoxide copolymer. Other examples of suitable nonionic dispersants finding use in the present invention are polysorbate 80 (also known as Tween® 80) or the Igepal® family of alkylphenoxypoly (ethyleneoxy)ethanols such as Igepal® CA-630. The dispersing agent can also comprise any mixture of the above mentioned examples including a siloxane polyalkyleneoxide copolymer, polysorbate 80, and an alkylphenoxypoly(ethyleneoxy)ethanol.

In a second suspension system, suspension system 2, according to the present invention the oil suspension of at least one of a microbe, a microbe derived metabolite or a combination thereof as described above is emulsified with an aqueous system to form a shelf stable and water dispersible suspension. The aqueous system used in suspension system 2 comprises the following components: water and, optionally, one or more of cyclodextrins, organic material such as humic acids for example CAS 1415-93-6, galactomannan polysaccharide emulsifier, at least one preservative such as sodium propionate or 1,2 benzisothiazol-3(2-H)-1, a yeast extract such as CAS 8013-01-2, glycerol, a nitrogen source such as urea, and mixtures thereof in the total amounts shown below in TABLE 2. The term cyclodextrin as is known to those of skill in the art refers to a family of cyclic oligosaccharides consisting of a macrocyclic ring of glucose subunits joined by alpha-1,4 glycosidic bonds. They are produced from starch by enzymatic activity. There are three main forms alpha-cyclodextrin has 6 glucose subunits, beta-cyclodextrin has 7 glucose subunits and gamma-cyclodextrin has 8 subunits. These three main types all find use in the present invention, either alone or in combination. Cyclodextrins have a toroidal type structure and the interior hole is hydrophobic while the exterior of the structure is hydrophilic, thus they can hold hydrophobic molecules in the interior space. Nutritional elements to aid plant germination and growth can also be supplied in this formulation. Examples of these nutritional elements include: leionardite, known to one of skill in the art to be a rich source of humic acid, up to 90% humic acids, CAS 1415-93-6; yeast extract CAS 8013-01-2; other microbial and botanical germination promoting extracts. Glycerol and other preservatives as described herein can be included in the formulation to further extend the shelf life in this otherwise aqueous formulation. The preferred ranges of the components of this second suspension system are shown below in TABLE 2. The wgt % is based on the total formulation weight and the cfu/ml level in the final formulation must be at least $10^8$ cfu/ml, however it can exceed this level as desired. The amount of water used is a sufficient amount to bring the formulation to 100 wgt %. All of the ranges include all ranges between the two ends of the range inclusively. An oil suspension of the microbes and/or metabolites is prepared as detailed herein and if used, the cyclodextrin(s) are combined with the oil suspension using a common stand mixer or stir plate. To prepare the suspension system 2, the water containing portion, which includes any optional components other than the cyclodextrin, is added to a blending container of an adjustable rotor-stator homogenizer capable of 10,000 to 29,000 rpm. The homogenizer is started and run at 10,000 to 29,000 rpm while the oil suspension, containing cyclodextrin(s) or not, is added to the blending container in a slow steady stream. This high shear mixing produces a stable emulsification of the oil suspension in suspension system 2 with the microbes remaining viable. The resulting suspension system 2 is shelf stable for more than 12 months a room temperature of approximately 25° C. and water dispersible. The suspension system 2 can consist essentially of the oil suspension as described, water and, optionally, one or more of cyclodextrins, organic material such as the humic acids, galactomannan polysaccharide emulsifier, at least one preservative, a yeast extract, glycerol, a nitrogen source, and mixtures thereof. Preferably, a suspension system 2 includes the one or more preservatives at 0.1 to 3 wgt % as noted below.

TABLE 2

| COMPONENT | FINAL FORMULATION AMOUNT |
|---|---|
| Oil suspension of microbes and/or microbial metabolites | 20 to 40 wgt % of the oil suspension providing in the final formulation $10^8$ cfu/ml or more, 0.08 to 2 wgt % metabolite |
| Cyclodextrin(s) | 0 to 10 wgt % |
| Water | 35 to 80 wgt % |
| Humic acids (CAS 1415-93-6) | 0 to 5 wgt % |
| Yeast extract (CAS 8013-01-2) | 0 to 5 wgt % |
| Glycerol | 0 to 20 wgt % |
| Preservative | 0.1 to 3 wgt % |
| Nitrogen, preferably from a source such as urea | 0 to 5 wgt % |
| Galactomannan polysaccharide emulsifier | 0 to 0.5 wgt % |

In a third suspension system, suspension system 3, according to the present invention the oil suspension of microbe, microbe derived metabolite or combination thereof can be combined with glycerol, a dispersion aid and, optionally, a galactomannan polysaccharide. The non-aqueous system used in this suspension system comprises the following components: an oil suspension of at least one of the microbe, a microbe derived metabolite, or a combination thereof; glycerol; a dispersant; and, optionally, galactomannan polysaccharide emulsifier in a total amount to reach 100% as shown below in TABLE 3. As would be clear to one of skill in the art, this suspension system can also be provided as a two component kit form with the first component being the oils suspension and the second component being the glycerol, dispersing agent and optional galactomannan polysaccharide. The kit would provide instructions for the mixing process and ratios to provide the required final formulation amounts as set forth in TABLE 3.

TABLE 3

| COMPONENT | FINAL FORMULATION AMOUNT |
|---|---|
| Oil suspension of microbes and/or microbial metabolites | 10 to 30 wgt % of the oil suspension providing in the final formulation $10^8$ cfu/ml or more, 0.04 to 1.5 wgt % metabolite |

TABLE 3-continued

| COMPONENT | FINAL FORMULATION AMOUNT |
|---|---|
| Glycerol | 66 to 89 wgt % |
| Dispersing agent | 1 to 3 wgt % |
| Galactomannan polysaccharide | 0 to 1 wgt % |

Figure 1B:
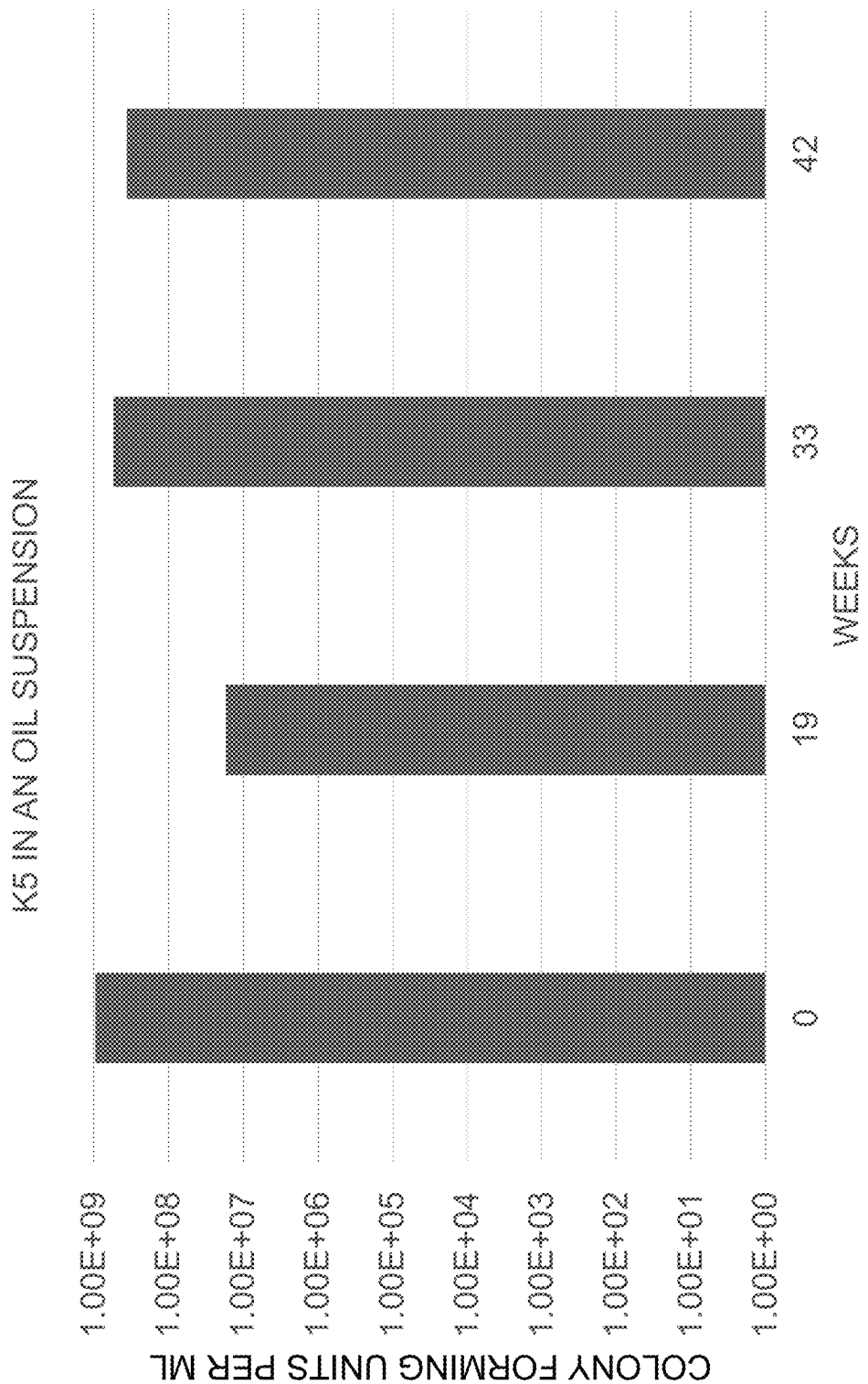
FIG. 1B is a graph showing the shelf stability over time of an oil suspension according to the present invention of the microbe *Trichoderma atroviride*, strain K5, stored at a temperature of from 22 to 25° C.
Figure 1C:
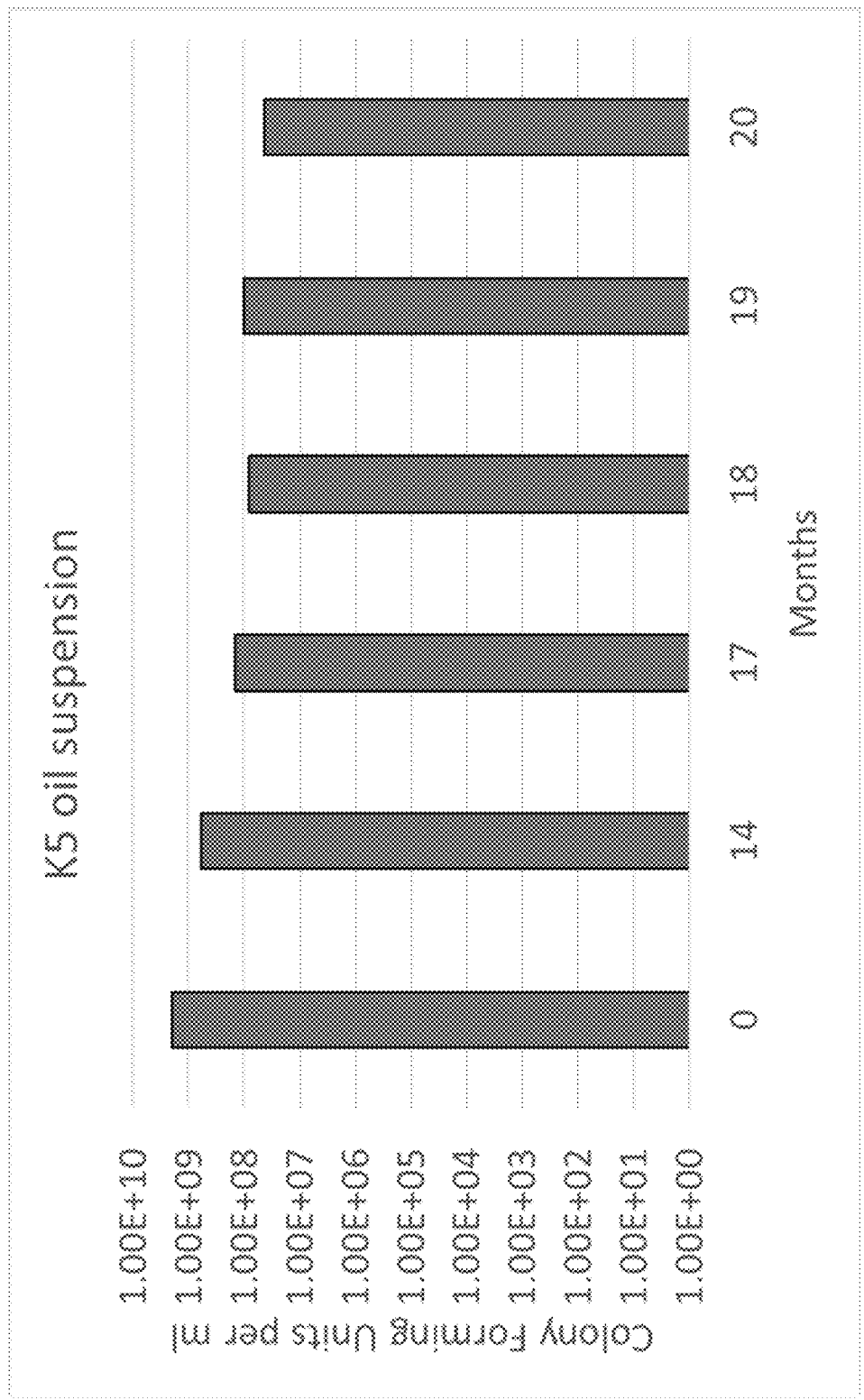
FIG. 1C is an additional graph showing the shelf stability over a longer period of time of an oil suspension according to the present invention of the microbe *Trichoderma atroviride*, strain K5, stored at a temperature of from 22 to 25° C.
Figure 1D:
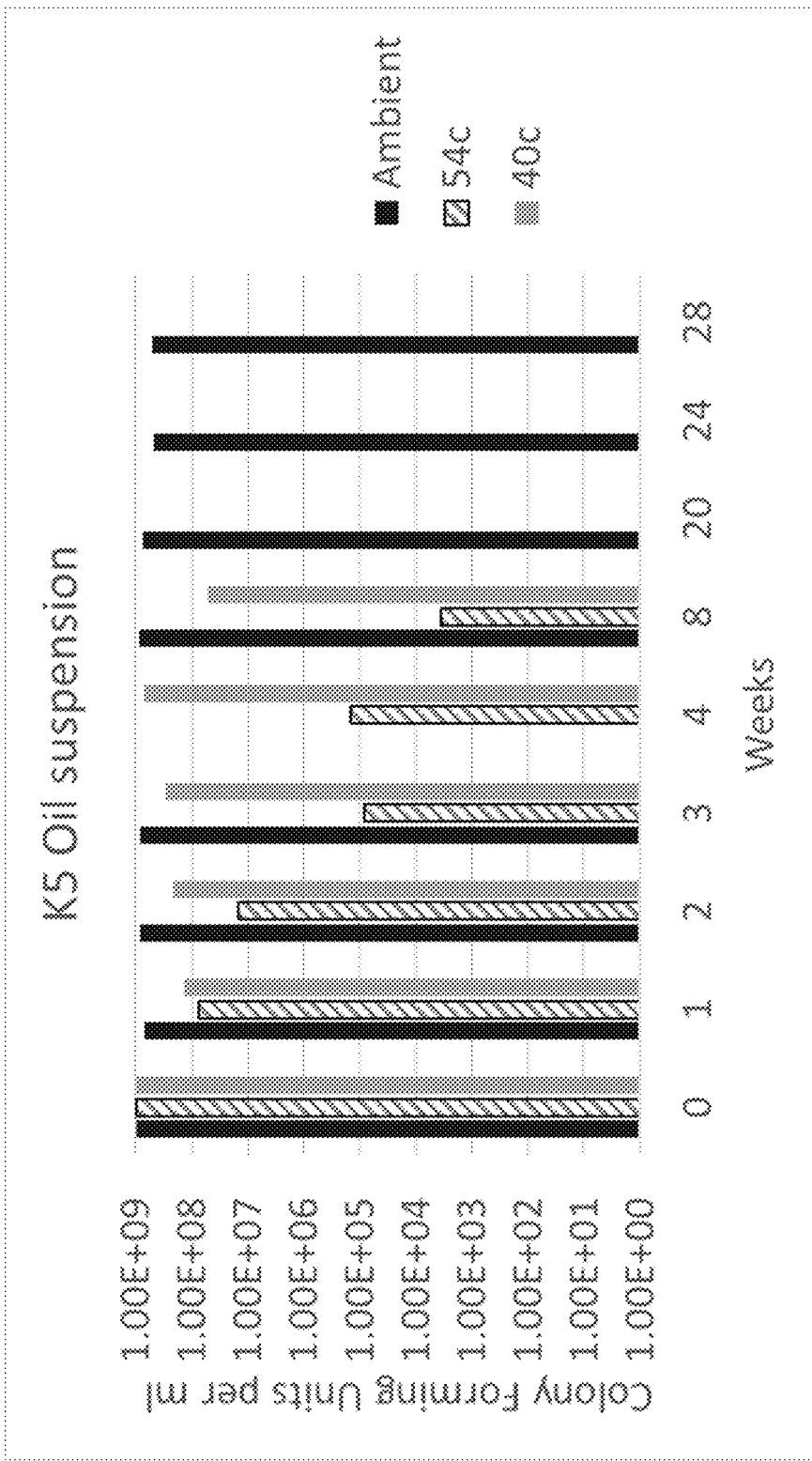
FIG. 1D is a graph showing the shelf stability over time at a series of temperatures for an oil suspension according to the present invention of the microbe *Trichoderma atroviride*, strain K5, stored at the indicated temperature, with ambient temperature being 22-25° C.

Referring in more detail to the drawings, FIG. 1A is a graph showing the shelf stability over time of an oil suspension according to the present invention of a combination of the microbes *Trichoderma afroharzianum*, strain K2, and *Trichoderma atroviride*, strain K4, suspended at a level of at least $10^8$ cfu/ml in oil and stored at a temperature of from 22 to 25° C. One sees the cfu/ml remains fairly stable over 44 weeks and is sufficient to provide a level of $10^8$ cfu/ml by the end of the period tested. In FIG. 1B is a graph showing the shelf stability over time of an oil suspension according to the present invention of the microbe *Trichoderma atroviride*, strain K5, stored at a temperature of from 22 to 25° C. Again one sees the cfu/ml remains fairly stable over 42 weeks and is sufficient to provide a level of $10^8$ cfu/ml by the end of the period tested. As shown in FIG. 1C, the shelf stability is maintained for at least 19 months at 22 to 25° C. The stability of this oil suspension is influenced by the storage temperature as shown in FIG. 1D. The oil suspension is stable at ambient temperature of 22-25° C. for an extended period as has been shown in this FIGS. 1D and 1C. Even at a storage temperature of 40° C., the oil suspension is stable for 8 weeks; however, as one raises the temperature to 54° C. the shelf stability falls more rapidly. At a storage temperature of 54° C. there are no viable spores after 8 weeks. In other experiments, data not shown, it was found that suspending the *Trichoderma atroviride* strain K5 in water alone at a temperature of 54° C. resulted in no viable spores regardless of the duration.

Figure 2A:
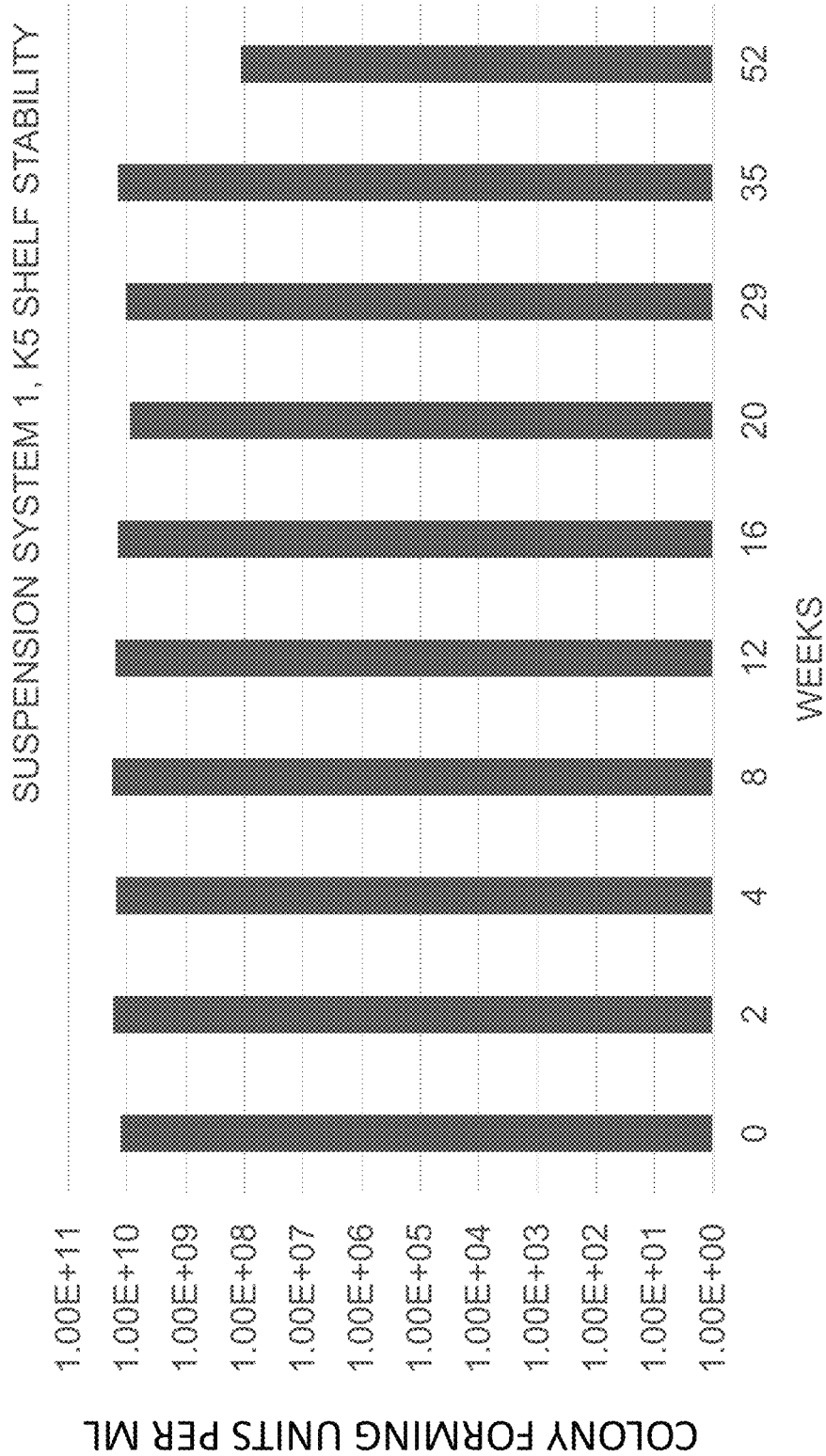
FIG. 2A is a graph showing shelf stability over time of *Trichoderma atroviride*, strain K5, prepared in suspension system 1 according to the present invention and stored at a temperature of from 22 to 25° C.

FIG. 2A is a graph showing shelf stability over time of *Trichoderma atroviride*, strain K5, prepared in suspension system 1 according to the present invention and stored at a temperature of from 22 to 25° C. As shown this suspension system 1 example began with a cfu/ml of $10^{10}$ cfu/ml at time 0. This was maintained for at least the first 35 weeks of storage. By week 53 this had dropped somewhat; however it was still above $10^8$ cfu/ml as required. Thus, suspension system 1 provides a shelf stability to the microbial solution of at least 52 weeks at a storage temperature of 22 to 25° C. Similar results are expected for other microbial species including those of particular interest in the present disclosure of: *Trichoderma virens; Trichoderma atroviride; Trichoderma afroharzianum; Trichoderma* K1; *Trichoderma* K2; *Trichoderma* K3; *Trichoderma* K4; *Trichoderma* K5; and mixtures thereof. All of the microbial metabolites 6-pentyl-pyrone; harzianic acid; the hydrophobic protein HYTRA 1; harzinolide; 1-octene-3-ol; and mixtures of these metabolites are also stable in the suspension systems according to the present disclosure.

Figure 2B:
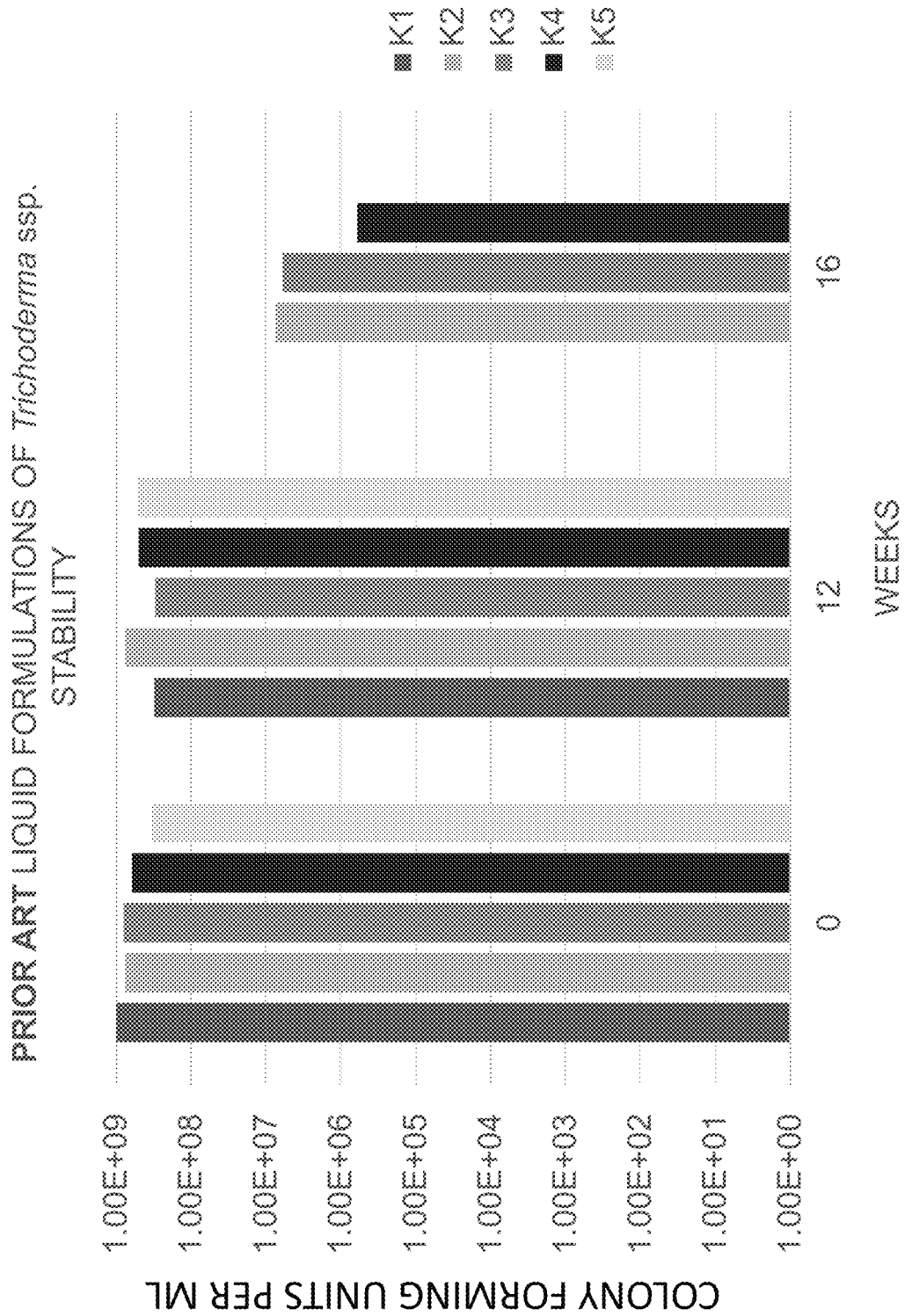
FIG. 2B is a graph showing shelf stability over time of PRIOR ART liquid formulations of a variety of *Trichoderma* spp. not prepared according to the present invention and stored at a temperature of from 22 to 25° C.

FIG. 2B is a graph showing shelf stability over time of PRIOR ART liquid formulations of a variety of *Trichoderma* spp. not prepared according to the present invention and stored at a temperature of from 22 to 25° C. The *Trichoderma* spp. used were K1, K2, K3, K4 and K5 as defined herein. These were prepared in liquid formulations not in accordance with the present invention. As a first matter this prior art formulation was not able to achieve as high of an initial cfu/ml as in suspension system 1. The initial, time 0, levels for all of the samples in this experiment was approximately $10^9$ to $5\times10^8$. All were able to maintain the cfu/ml at above $10^8$ cfu/ml for the first 12 weeks. By week 16 none of the prior art samples were able to maintain the cfu/ml at an acceptable level. The samples containing K1 and K5 had no viable spores by week 16 and the samples with K2, K3 and K4 were all far below the acceptable $10^8$ cfu/ml by week 16. Thus, the data in FIGS. 2A and 2B show how superior the present suspension system 1 is to the prior art systems in maintaining the viability of the microbes.

Figure 3A:
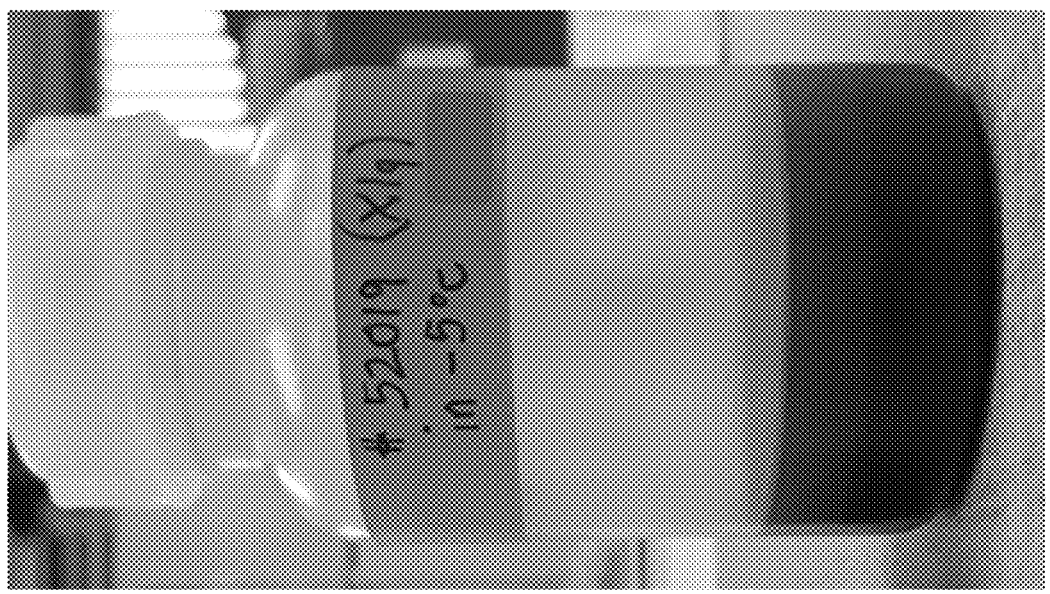
FIG. 3A is a photograph showing phase stability of *Trichoderma atroviride*, strain K5, prepared in suspension system 1 according to the present invention and stored at a temperature of −5° C. for 1 week.
Figure 3B:
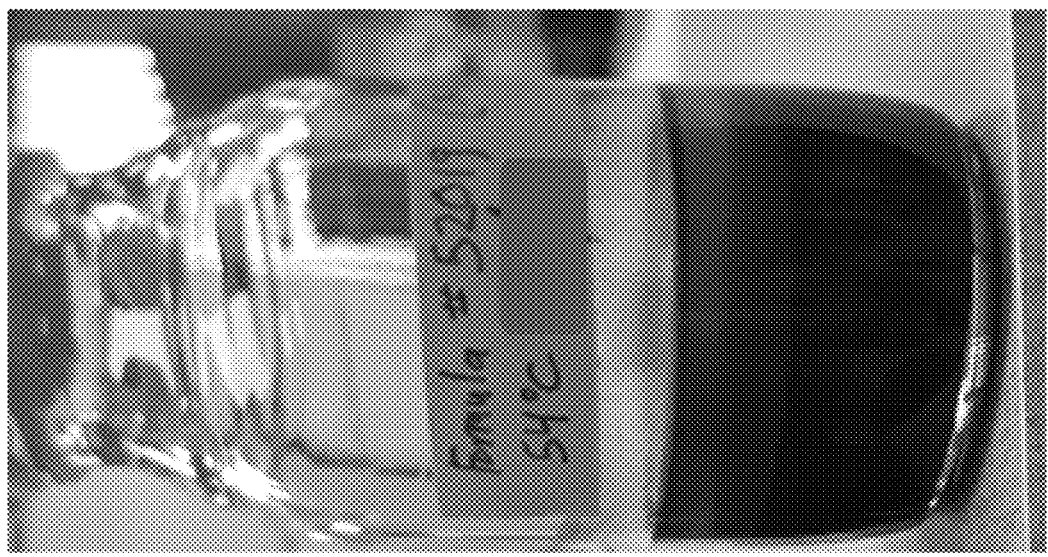
FIG. 3B is a photograph showing phase stability of *Trichoderma atroviride*, strain K5, prepared in suspension system 1 according to the present invention and stored at a temperature of 54° C. for 2 weeks.
Figure 3C:
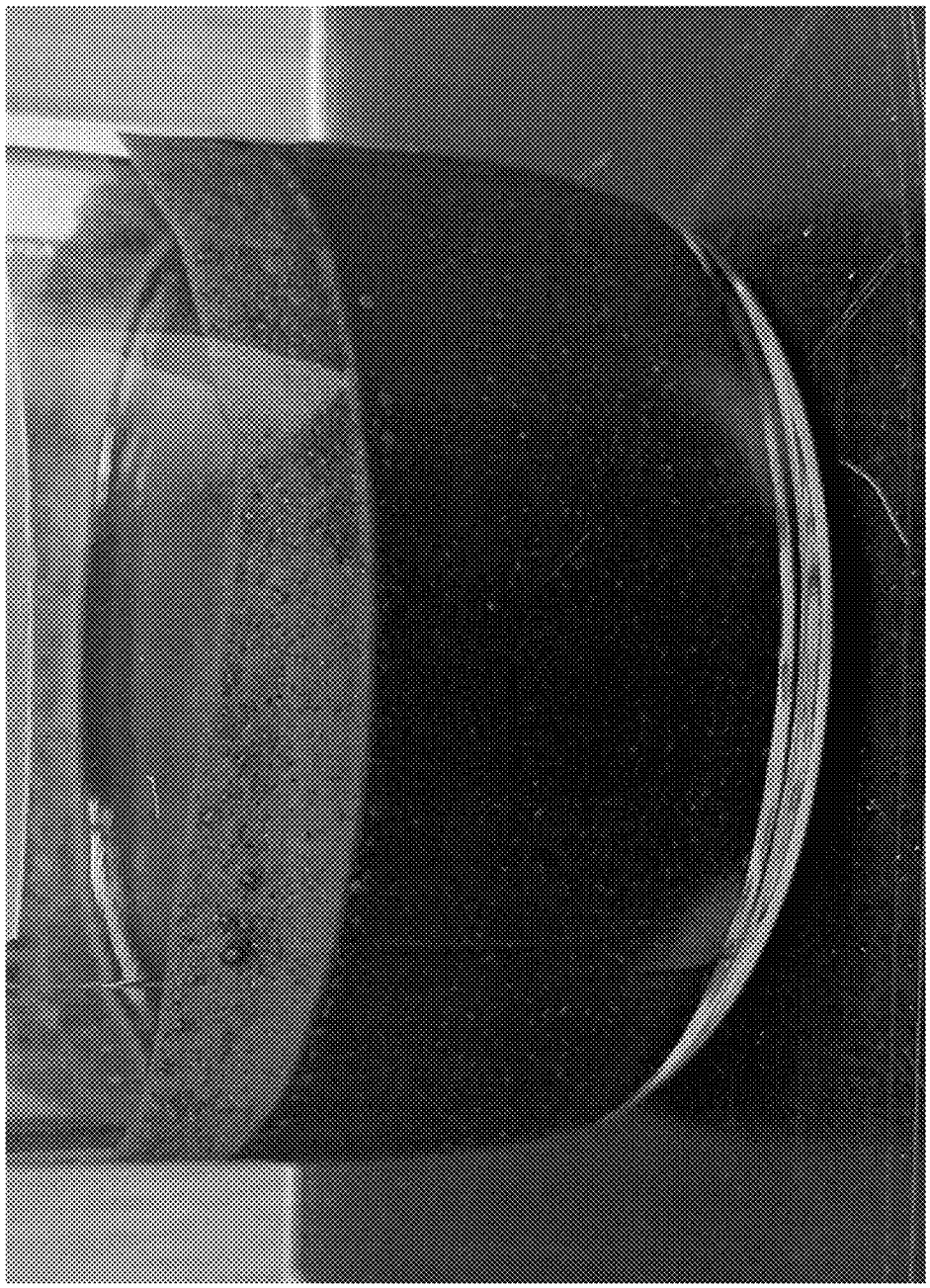
FIG. 3C is a photograph show phase stability of suspension system 2 containing $10^9$ cfu/ml of *Trichoderma atroviride*, strain K5, prepared in suspension system 2 according to the present invention stored at a temperature of 25° C. for 3 weeks.

FIG. 3A is a photograph showing phase stability of *Trichoderma atroviride*, strain K5, prepared in suspension system 1 according to the present invention and stored at a temperature of −5° C. for 1 week. FIG. 3B is a photograph showing phase stability of *Trichoderma atroviride*, strain K5, prepared in suspension system 1 according to the present invention and stored at a temperature of 54° C. for 2 weeks. FIG. 3C is a photograph show phase stability of suspension system 2 containing *Trichoderma atroviride*, strain K5, at $10^9$ cfu/ml according to the present invention stored at a temperature of 25° C. for 3 weeks.

The photographs of FIG. 3A-3C show the lack of phase separation of the two suspension systems according to the present invention over time at various temperatures. Similar phase stability is seen for suspension system 1 or 2 containing microbial metabolites. One can see that there is no phase separation in any of the samples. In addition, although not shown when phase separation does occur it is not irreversible and the single phase can be restored by inverting the container several times.

Figure 4A:
FIG. 4A is a photograph of the PRIOR ART liquid formulation of a combination of the microbes *Trichoderma afroharzianum*, strain K2, and *Trichoderma atroviride*, strain K4, not according to the present invention after 8 hours of sitting undisturbed at room temperature following dilution of a solution containing $10^9$ cfu/ml of each microbe at a volume ratio of 1:127 in reverse osmosis water with stirring.
Figure 4B:
FIG. 4B is a photograph of suspension system 1 containing *Trichoderma atroviride*, strain K5, prepared in suspension system 1 according to the present invention after 8 hours of sitting undisturbed at room temperature following dilution of a solution of $10^9$ cfu/ml at a volume ratio of 1:127 in reverse osmosis water with stirring.
Figure 4C:
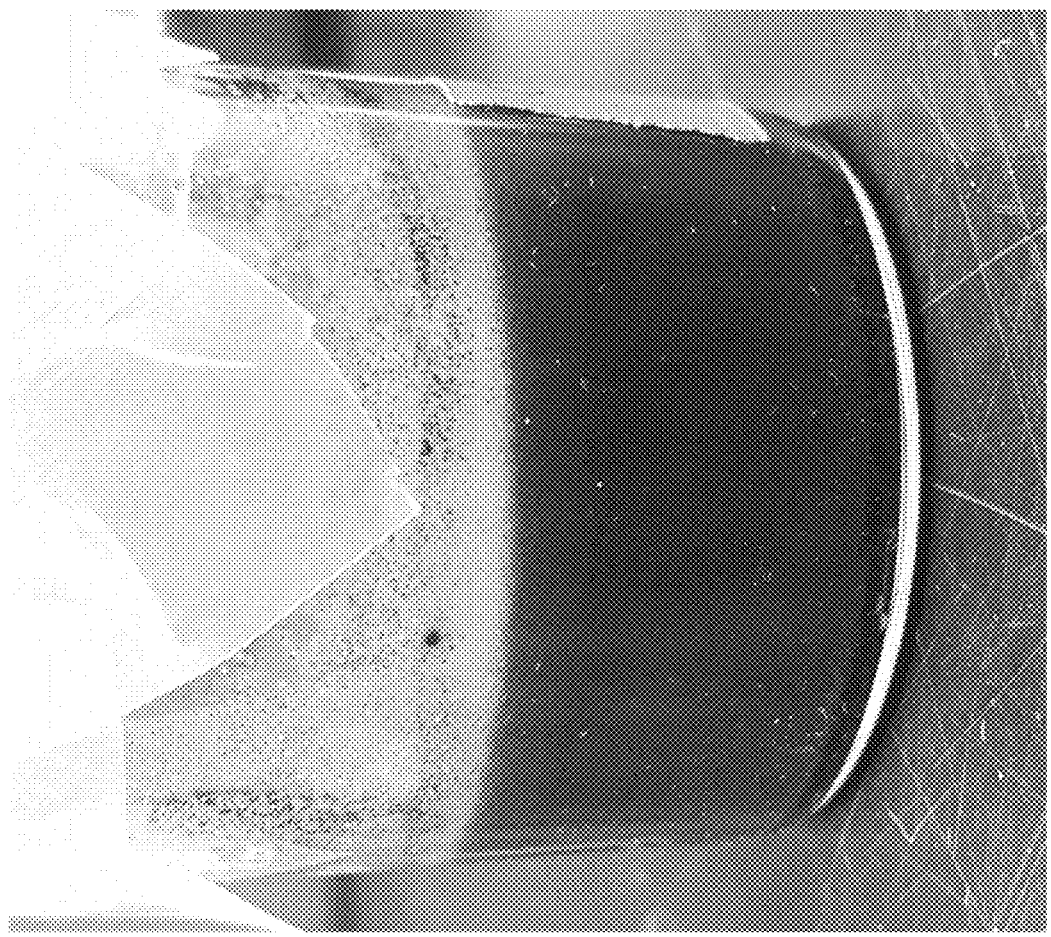
FIG. 4C is a photograph of suspension system 2 containing the microbial metabolite 1-octene-3-ol according to the present invention after 8 hours of sitting undisturbed at room temperature following dilution of a solution containing 0.86% by weight of 1-octene-3-ol based on the total suspension system weight at a volume ratio of 1:127 in reverse osmosis water with stirring.

FIG. 4A is a photograph of the PRIOR ART liquid formulation of a combination of the microbes *Trichoderma afroharzianum*, strain K2, and *Trichoderma atroviride*, strain K4, not according to the present invention after 8 hours of sitting undisturbed at room temperature following dilution of a solution having $10^9$ cfu/ml of each strain at a volume ratio of 1:127 in reverse osmosis water with stirring. FIG. 4B is a photograph of suspension system 1 according to the present invention containing *Trichoderma atroviride*, strain K5, after 8 hours of sitting undisturbed at room temperature following dilution of $10^9$ cfu/ml at a volume ratio of 1:127 in reverse osmosis water with stirring. FIG. 4C is a photograph of suspension system 2 containing 1-octene-3-ol according to the present invention after 8 hours of sitting undisturbed at room temperature following dilution of suspension system 2 containing 0.86% by weight based on the total suspension weight of 1-octene-3-ol at a volume ratio of 1:127 in reverse osmosis water with stirring. One can see that a suspension system, either suspension system 1 or suspension system 2, according to the present invention, after dilution in water, demonstrates complete miscibility of the suspension system in the water. By way of contrast as shown in FIG. 4A, the PRIOR ART system shows a clear demarcation of phase separation with a darker lower layer and a lighter upper layer. This again demonstrates the superiority of the suspension systems according to the present invention compared to the prior art systems.

A suspension prepared according to suspension system 1 of the present invention has the physical characteristics shown below in TABLE 4.

TABLE 4

| PHYSICAL PROPERTY | CHARACTERISTIC |
|---|---|
| Density | 0.99 gm/ml |
| Miscibility | Water dispersible |
| Corrosiveness | Non-corrosive in any packaging materials |
| pH | Approximately 7 |

TABLE 4-continued

| PHYSICAL PROPERTY | CHARACTERISTIC |
|---|---|
| Seed flowability | No impact on it due to low levels of use |
| Dust off | No impact due to low levels of use |
| Phase separation | None at room temperature storage, none after freezing, some after storage at 54° C., however it is not irreversible and a single phase is restored after inversion of the container several times |
| Color | Depends on the identity of the microbe. |
| Physical state | Liquid |
| Odor | Earthy |
| Shelf stability | Expected to be at least 2 years if stored at 5 to 35° C. |
| Freeze/Melt point | −18° C. |
| Post-freezing attributes | No change in formulation attributes |
| Atomization competence | Competent, no change in spore viability after atomization |

Figure 5:
FIG. 5 is a photograph of an oil suspension of *Trichoderma afroharzianum*, strain K2, according to the present invention after plating and growth on a non-selective medium, there are no contaminating microbes evident.
Figure 6:
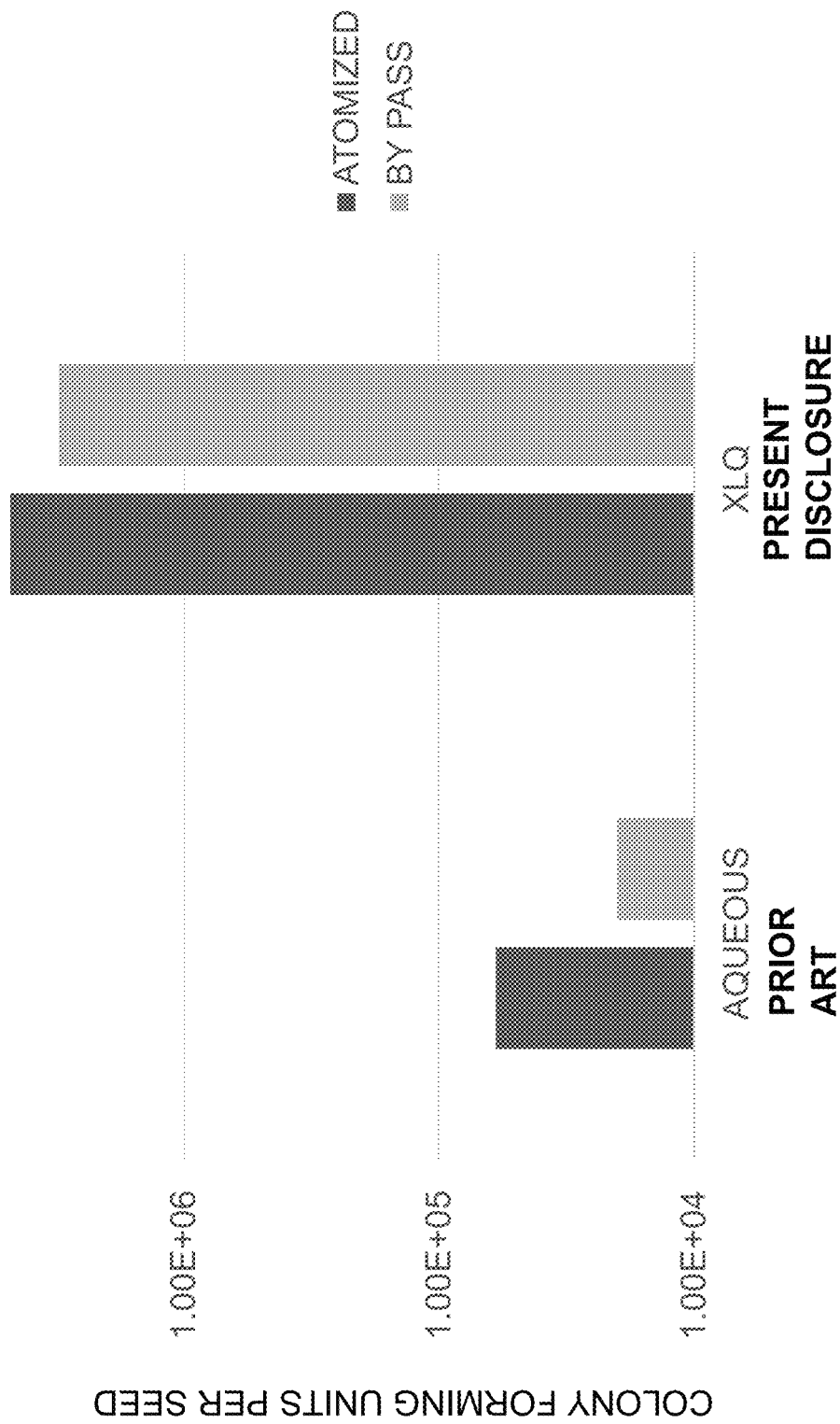
FIG. 6 is a graph showing the ability to coat seeds with colony forming units following application to the seeds by either atomization (ATOMIZED) or direct application (BY PASS), of either the PRIOR ART liquid formulation not according to the present invention comprising a mixture of the microbes *Trichoderma afroharzianum*, strain K2, and *Trichoderma atroviride*, strain K4, both at a level of $10^9$ cfu/ml in the formulation and designated by the legend AQUEOUS PRIOR ART in the figure or suspension system 1 according to the present invention containing *Trichoderma atroviride*, strain K5, at a level of $10^9$ cfu/ml and designated by the legend XLQ PRESENT DISCLOSURE in the figure.
Figure 7:
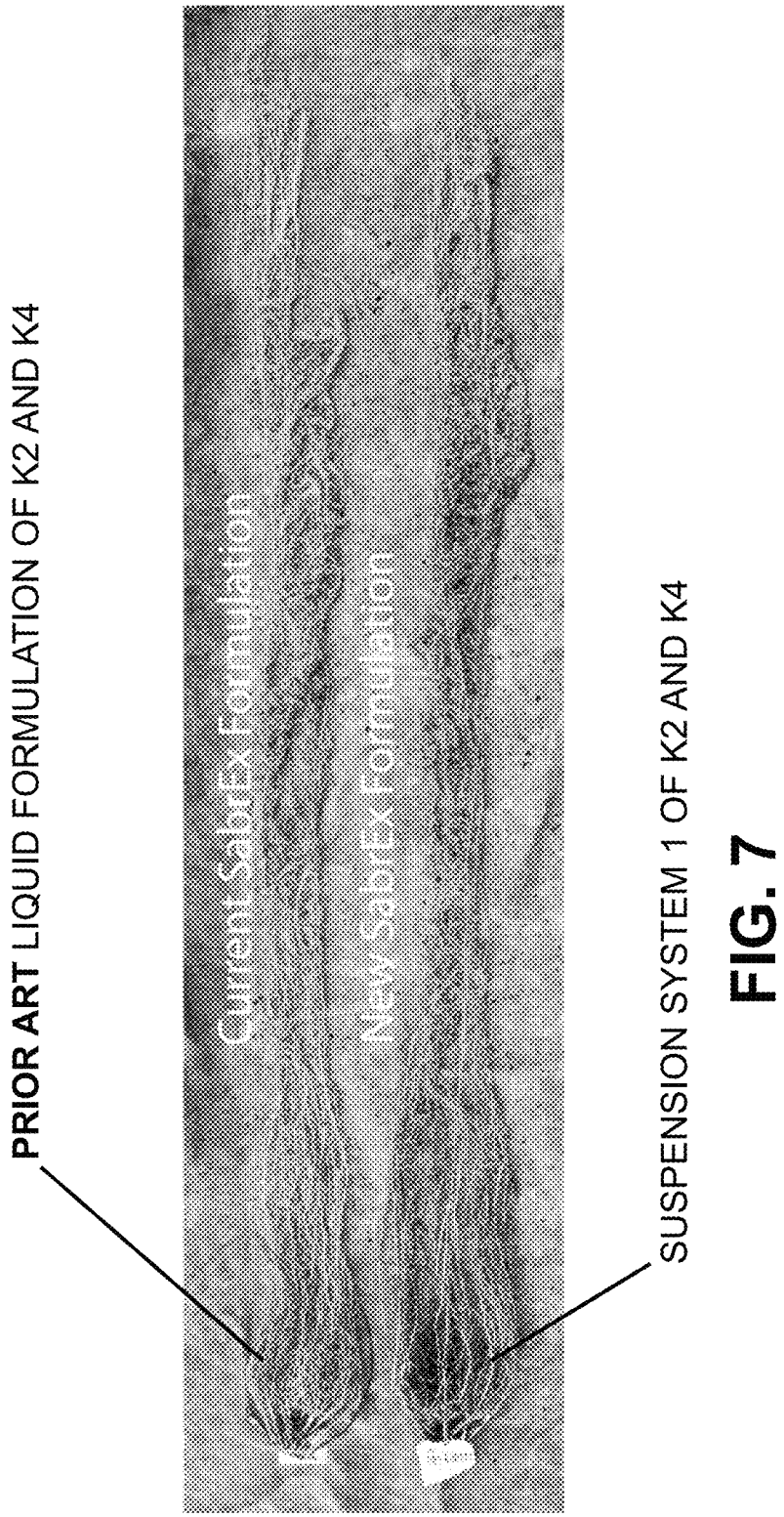
FIG. 7 is photograph showing a side by side comparison of the root system for corn plants following treatment of the seeds with a combination of the microbes *Trichoderma afroharzianum*, strain K2, and *Trichoderma atroviride*, strain K4, suspended in either the aqueous formulation according to the PRIOR ART, top photograph, or in suspension system 1 according to the present invention, bottom photograph.
Figure 8:
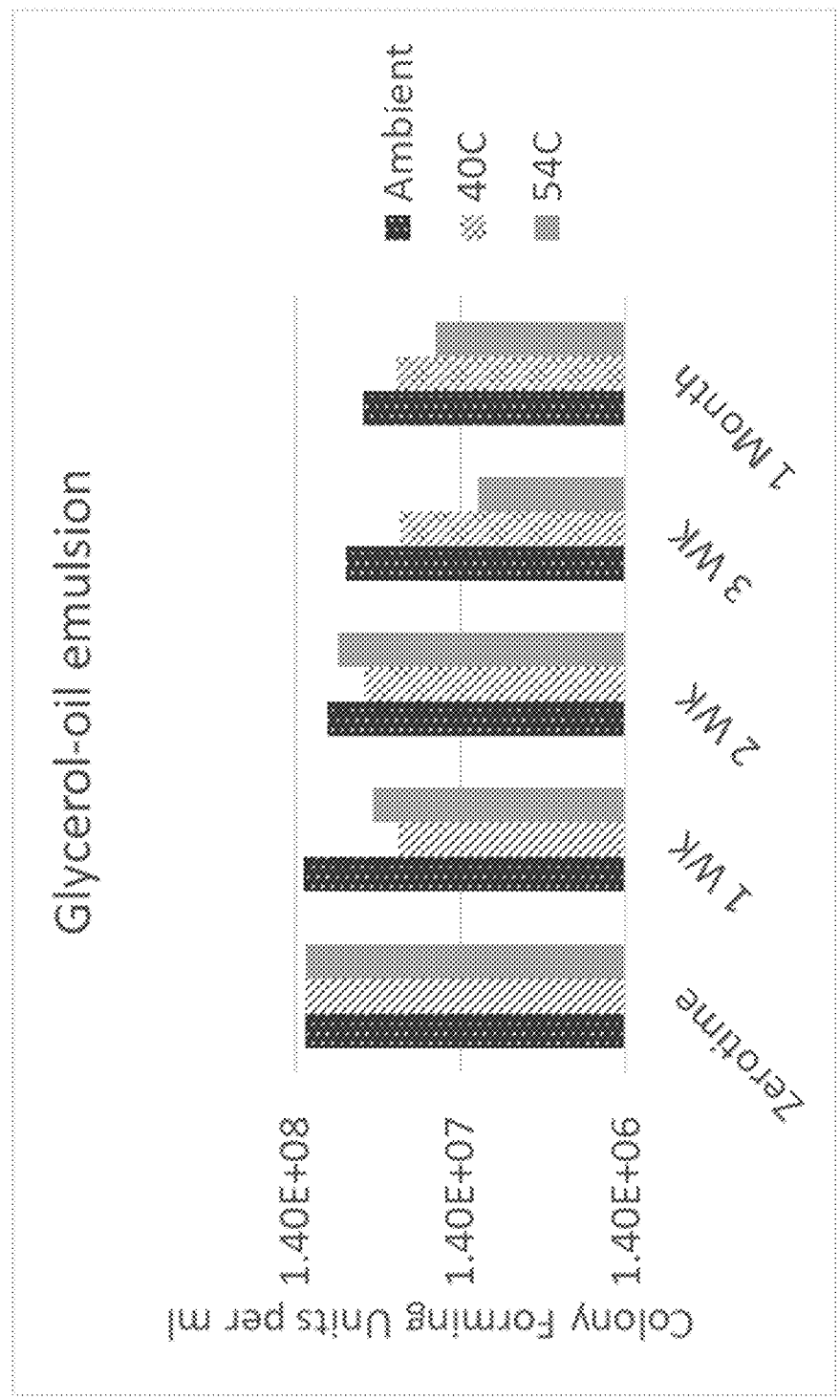
FIG. 8 is a graph showing the shelf stability over time at a series of temperatures for suspension system 3 according to the present invention of the microbe *Trichoderma atroviride*, strain K5, stored at the indicated temperatures, ambient temperature being 22-25° C.
Figure 9B:
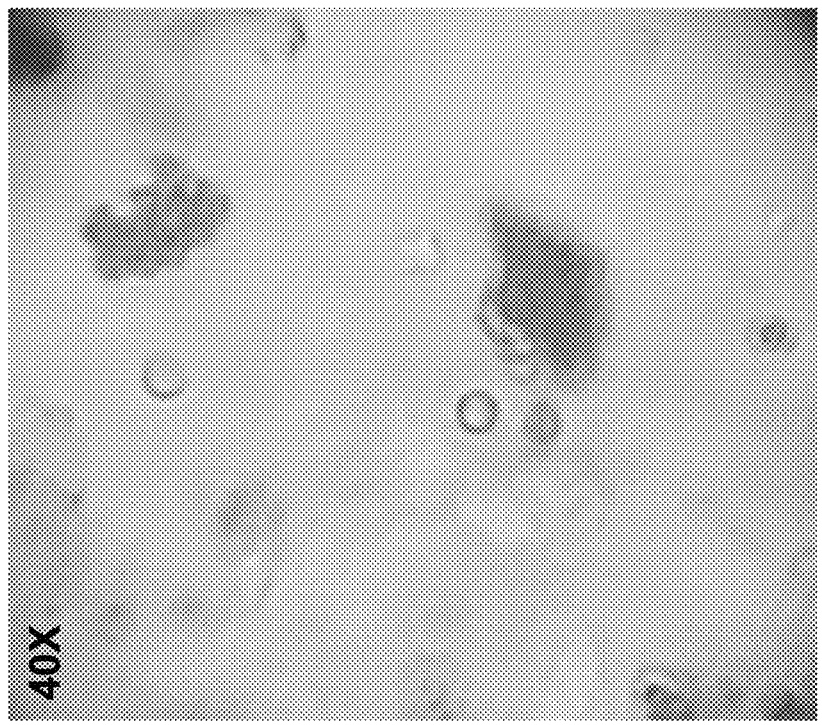
FIGS. 9A and 9B are photographs of 1:1 volume dilutions in reverse osmosis water of suspension system 3 according to the present invention of the microbe *Trichoderma atroviride*, strain K5, at magnifications of 10× and 40× respectively showing clumping of the spores.
Figure 9A:
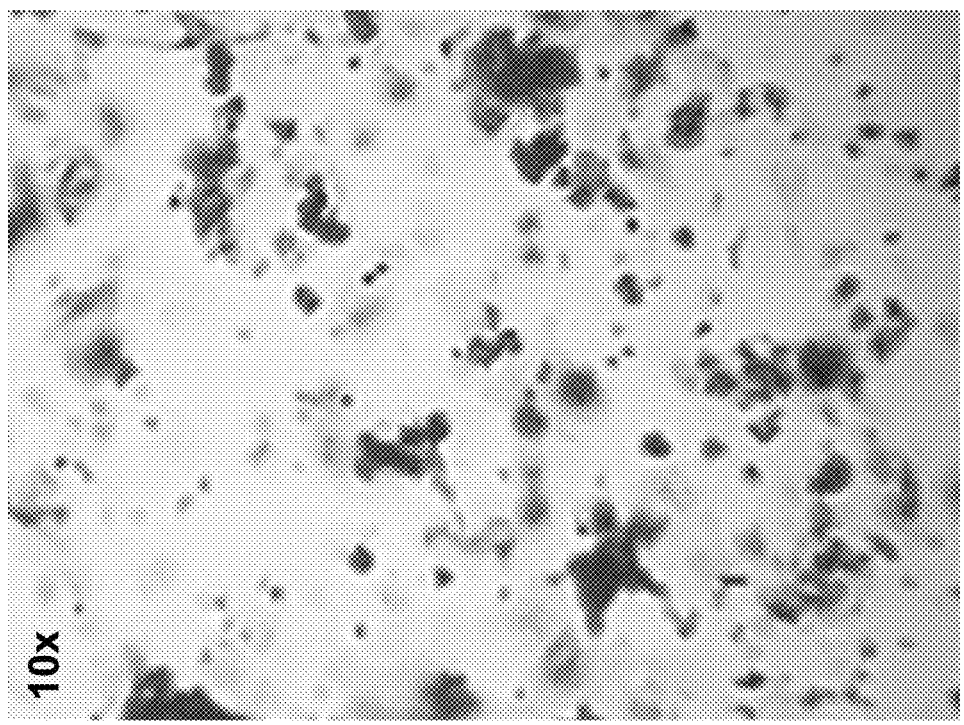

FIG. 5 is a photograph of an oil suspension of *Trichoderma afroharzianum*, strain K2, according to the present invention after plating and growth on a non-selective medium to test for the presence of contaminates. The plate was a potato dextrose agar plate supplemented with Igepal® CA-630 and it was plated with a dilution of the oil suspension by the spreading method. Potato dextrose is a rich medium on which both fungal species and bacterial species readily grow. The Igepal® was included in the growth medium because it is known to restrict the growth of *Trichoderma* colonies and thus its presence will enable the visualization of slower growing contaminants. The figure shows that only *Trichoderma* colonies were formed on the plate indicating no contaminants were present. Similar results are seen for suspension system 1 and suspension system 2 containing the *Trichoderma* spp. when plated out in the same system.

FIG. 6 is a graph showing the ability to coat seeds with colony forming units following application to the seeds by either atomization (ATOMIZED) or direct application (BY PASS), of either the PRIOR ART liquid formulation not according to the present invention comprising a mixture of the microbes *Trichoderma afroharzianum*, strain K2, and *Trichoderma atroviride*, strain K4, both at a level of $10^9$ cfu/ml in the formulation and designated by the legend AQUEOUS PRIOR ART in the figure or suspension system 1 according to the present invention containing *Trichoderma atroviride*, strain K5, at a level of $10^9$ cfu/ml and designated by the legend XLQ PRESENT DISCLOSURE in the figure. These results were obtained using a Hege lab scale seed treating system. The formulations were diluted to tank strength mixtures with water and passed over a spinning disc. The results show that the suspension system 1 according to the present invention can coat the seeds to a much higher level of cfu per seed compared to the prior art formulation. In addition, the suspension system 1 according to the present invention was equally effective if applied by atomization or directly to the seeds. By way of contrast the prior art had much lower application of cfu per seed and there was a marked difference between the atomization method and the direct application with the latter be much less effective.

FIG. 7 is photograph showing a side by side comparison of the root system for corn plants following treatment of the seeds with a combination of the microbes *Trichoderma afroharianum*, strain K2, and *Trichoderma atroviride*, strain K4, suspended in either the aqueous formulation according to the PRIOR ART, top photograph, or in suspension system 1 according to the present invention, bottom photograph. *Trichoderma* strains K2 and K4 were formulated either in the aqueous formulation ($10^9$ cfu/ml) or in suspension system 1 ($10^9$ cfu/ml). Corn seeds were treated with each solution to achieve approximately $10^4$ cfu/seed and planted into a field soil/soilless mix in 8" diameter 7' PVC pipes that were embedded in the ground. Each treatment was planted into 4 tubes which were randomized amongst other treatments not relevant to the current application. Plants were maintained throughout the growing season and harvested as is typical for field corn production. The tubes were removed from the ground, disassembled and the soil washed from the roots to enable data collection. The photographs in FIG. 7 show the washed roots of representative tubes for the PRIOR ART aqueous formulation vs suspension system 1. The top photograph shows the PRIOR ART aqueous formulation. As shown in the figure, the roots from seeds treated with suspension system 1 were less readily washed free of soil owing to greater root hair/fibrous root development and biomass. This suggests that there may be a heightened efficacy of seeds treated with suspension system 1 according to the present invention.

In FIG. 8 is a graph showing the shelf stability over time at a series of temperatures for suspension system 3 according to the present invention of the microbe *Trichoderma atroviride*, strain K5, stored at the indicated temperatures, with ambient temperature being 22-25° C. See TABLE 7 for the formulation of this suspension system 3. As shown in the data whether at ambient temperature or 40° C. the K5 spores showed similar viability for an extended period of time. The suspension stored at 54° C. showed a drop in viability by 1 month. One characteristic of this suspension system 3 is that there is significant clumping of the spores and adhesion to each other. This is shown for example in the photographs of FIGS. 9A and 9B. Accurate counting of viable cells requires use of a dispersant when dilution plating, which was not done in the photos shown in FIGS. 9A and 9B.

FIG. 11 is a graph showing survival on peanut seeds of *Bradyrhizobium* spp. or *Trichoderma atroviride* strain K5 wherein the microbes were either suspended in an aqueous solution (aq) not in accordance with the present disclosure or in the two component embodiment of suspension system 1 (SS1) according to the present invention as described herein and then applied to the seeds and dried. The *Bradyrhizobium* spp. are commonly found nodulating on peanut seeds and they were at a level of $1\times10^{10}$ cfu/ml in the application medium. The data shows that the microbes applied using a suspension system according to the present disclosure remain viable over time after application to seeds. The microbes were viable for at least an additional month compared to the aqueous control application. Given the typical field use schedule, 4 months of seed viability post seed treatment is compatible with treatment and planting schedules such that effective nodulation can be achieved during the growing season. The two component suspension system 1 was tested using *Trichoderma atroviride* strain K5 as a point of use blend to determine its efficacy in combination with *rhizobia* peanut inoculants. This was implemented as The 2 Component Suspension System 1, with Component 1 being:

| COMPONENT | FINAL FORMULATION AMOUNT |
|---|---|
| Canola oil | 93.8 wgt % |
| *Trichoderma* spores | 6.19 wgt % |

And component 2 being:

| COMPONENT | FINAL FORMULATION AMOUNT |
| --- | --- |
| Guar gum | 1.33 wgt % |
| Glycerol | 23.9 wgt % |
| Sodium proprionate | 0.93 wgt % |
| Reverse Osmosis H$_2$O | 73.84 wgt % |

Figure 11:
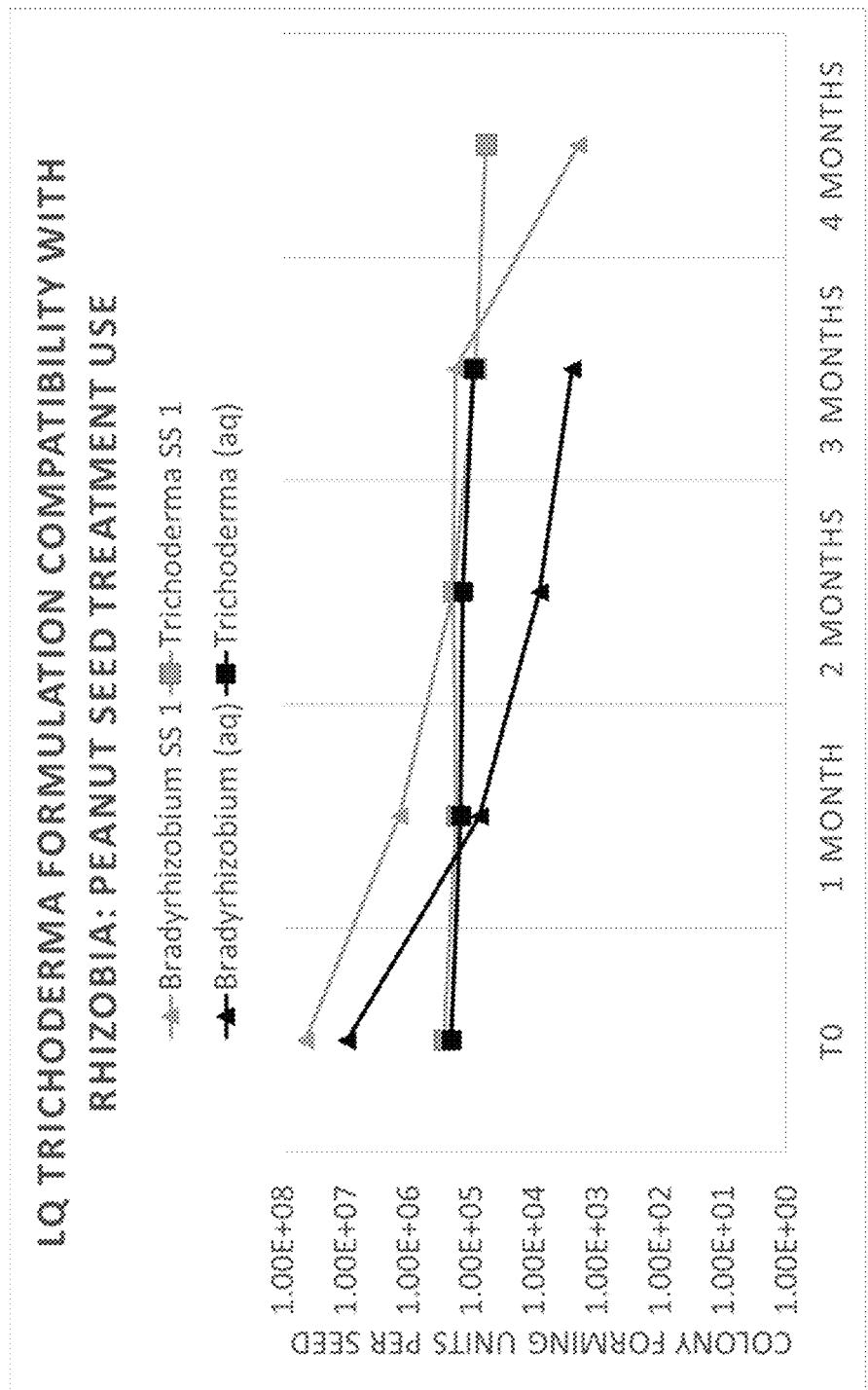
FIG. 11 is a graph showing survival on peanut seeds of *Bradyrhizobium* spp. or *Trichoderma atroviride* strain K5 wherein the microbes were either suspended in an aqueous solution (aq) not in accordance with the present disclosure or in a two component embodiment of suspension system 1 (SS1) according to the present invention, applied to the seeds and dried prior to testing at the indicated times.
Figure 12:
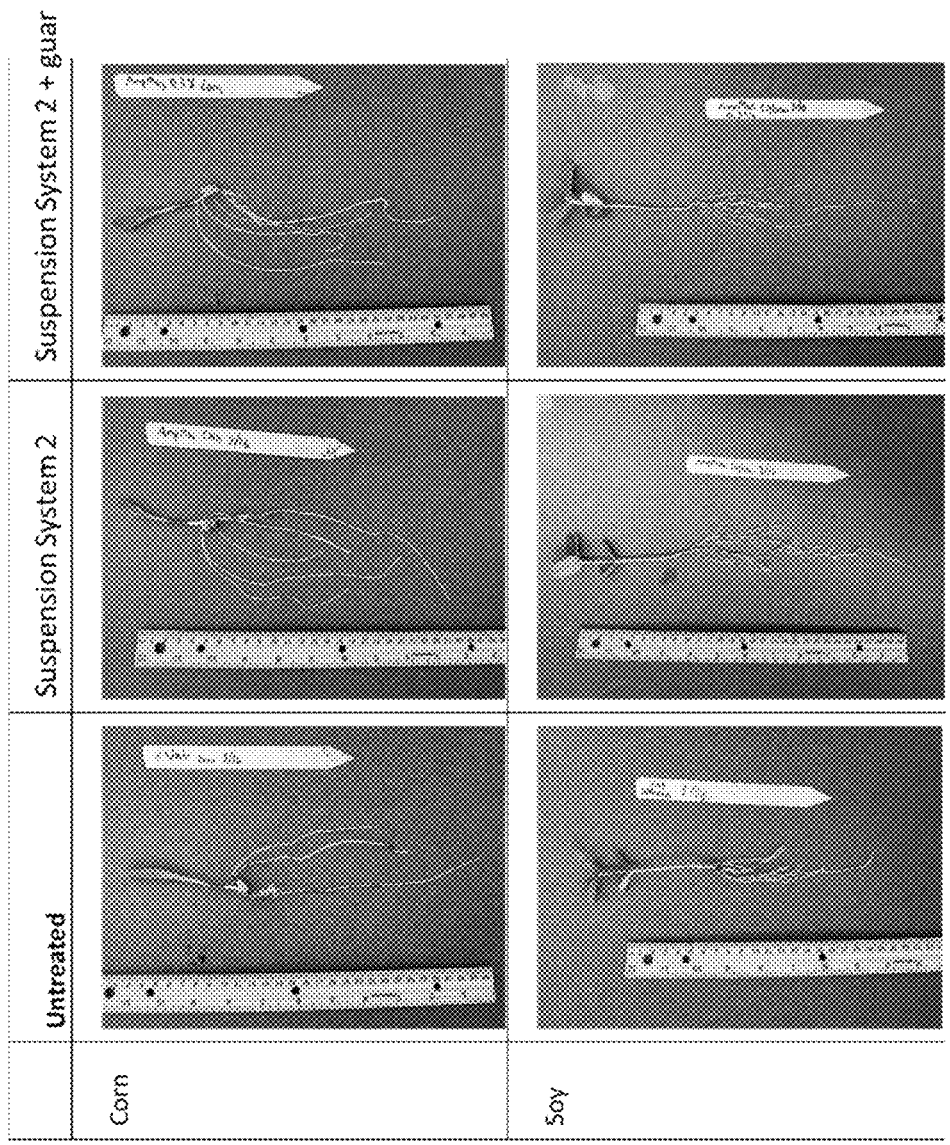
FIG. 12 is a series of panels of photographs of plants grown from corn or soybean seeds that were either untreated, treated with suspension system 2 according to the present disclosure containing no galactomannan (Suspension System 2) or treated with suspension system 2 according to the present disclosure containing galactomannan (Suspension System 2+guar).

Components 1 and 2 were mixed 1:1 by volume and added to a tank mix with a liquid *Bradyrhizobium* ssp. solution containing 1×10$^{10}$ cfu/ml. The tank mix contained 0.4 fl oz Component 1, 0.4 fl oz Component 2, and 2 fl oz *Bradyrhozobium* liquid per 100 lbs peanut seed. The total volume of the tank mix was 5 fl oz per 100 lbs peanut seed, with the remainder being reverse osmosis H$_2$O. One pound of seed was treated and therefore 0.05 fl oz of tank mix was added to a resealable plastic bag along with 1 lb seed, the bag sealed, and shaken vigorously for 1 minute to thoroughly coat the seeds. The CFUs per seed were evaluated on the day of seed treatment and monthly through 4 months post treatment. Seed washes were performed by placing 10 seeds in 10 ml sterile reverse osmosis H$_2$O and vigorously vortexing for 90 seconds. The number of cfus/ml in the resultant solution are reflective of the number of cfus/seed. This solution was subjected to a 10× dilution series and plated on acidified potato dextrose agar (PDA) supplemented with Igepal® CA-630. PDA is a rich microbial medium that is a typical growth medium for assaying *Trichoderma* viability. Acidification was achieved by the addition of tartaric acid to a final concentration of 0.17%. Igepal® CA-630 was added at 0.1% to restrict *Trichoderma* colony growth to achieve discrete, countable colonies. Data are presented in FIG. 11 showing *Trichoderma* survivability similar to aqueous formulation performance over 3 months and superior survivability of *Bradyrhizobium* with the 2 component suspension system 1. After two months, the aqueous system was not monitored further and it is notable that the 2 component suspension system 1 enables an additional month of on seed shelf life as compared with an aqueous only application.

In an example of use of the suspension system 2 according to the present invention a series of suspensions were prepared as detailed in TABLE 5 below, the microbe derived metabolite was suspended in the oil. Suspension A did not include the galactomannan guar gum while Suspension B did.

TABLE 5

| COMPONENT | SUSPENSION A Weight % | SUSPENSION B Weight % |
| --- | --- | --- |
| Soybean oil | 23.1 | 23.1 |
| Humic acid (CAS 1415-93-6) | 1.305 | 1.305 |
| Yeast extract (CAS 8013-01-2) | 1.631 | 1.631 |
| Glycerol | 13.051 | 13.051 |
| Cyclodextrin | 8.979 | 8.979 |
| 1-octene-3-ol | 0.036 | 0.036 |
| Sodium propionate | 0.653 | 0.653 |
| Urea (46% N) | 3.552 | 3.552 |
| Guar gum | 0.0 | 0.300 |
| Water | 47.694 | 47.394 |

Figure 10:
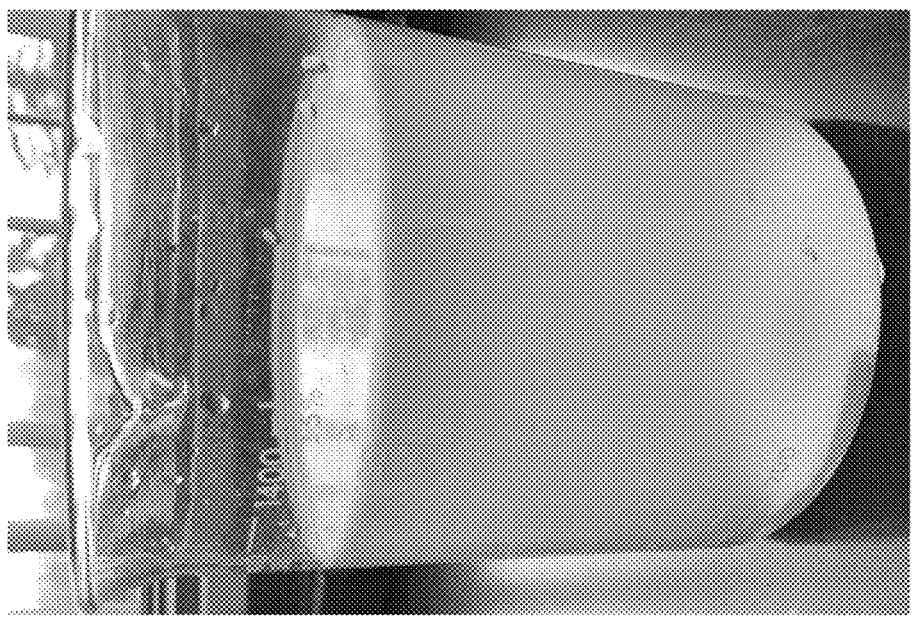
FIG. 10 is a photograph showing a tank mix of a suspension system according to the present disclosure.

Tank mix testing in water was performed using a dilution of 1:15 (suspension:water) for each of the SUSPENSION A and SUSPENSION B. The guar gum containing formulation SUSPENSION B showed that this suspension system generates an excellent tank mix in water as shown in FIG. 10. The FIG. 10 shows that the suspension system fully disperses in the water dilution thereby ensuring even application to seeds, in furrow, to soil, foliar spray application and other methods of application. Similar results are seen for the other suspension systems according to the present disclosure. The resultant tank mixes were used to treat corn, soybean and peanut seeds which were then subjected to a soil based germination test in the greenhouse. Seed treatment was performed by adding a given tank mix to seeds and mixing in a plastic resealable bag and shaking vigorously for 1 minute. Suspension system 2 application rates used were as follows: Corn received 0.1 fl oz/80,000 seeds, soybeans received 0.1 fl oz/140,000 seeds, and peanuts received 0.1 fl oz oz/50 lbs seed.

Significant improvements in germination were seen for all crops tested and for both versions of this suspension system 2 test. The germination rate results are shown in TABLE 6.

TABLE 6

| Plant seeds | Untreated | Suspension A | Suspension B |
|---|---|---|---|
| Corn | 71% | 93% | 85% |
| Soybeans | 76% | 90% | 95% |
| Peanuts | 58% | 67% | 75% |

FIG. 12 is a series of panels of photographs of plants grown from the corn or soybean seeds that were either untreated, treated with suspension system 2 SUSPENSION A according to the present disclosure containing no galactomannan (Suspension 2) or treated with suspension system 2 SUSPENSION B according to the present disclosure containing galactomannan (Suspension System 2+guar). One sees that the root growth is enhanced with either of the suspension system 2 treatments according to the present invention compared to the untreated seeds. Seeds treated with either formulation of suspension system 2 had an increased root biomass compared to the untreated control.

An example of suspension system 3 was prepared as shown in TABLE 7:

TABLE 7

| COMPONENT | FINAL FORMULATION AMOUNT |
|---|---|
| Canola oil spore suspension | 20 wgt % |
| Glycerol | 78 wgt % |
| Tween 80 | 2 wgt % |

The canola oil spore suspension contained $6.63\times10^8$ cfu/ml of *Trichoderma atroviride* K5 dry spores resulting in a final formulation that was $1.33\times10^8$. This system creates an oil in glycerol emulsion in which the spores are not exposed to water. FIG. 8 demonstrates the spore viability over time in this formulation through 1 month at various temperatures. It is anticipated that because this is a non-aqueous formulation similar to a simple oil suspension of spores (used in suspension system 1) the shelf life will also be well over 1 year. Further FIG. 8 shows that at the 1 month timepoint, spore survivability in suspension system 3 is superior to the oil suspension (FIG. 1D) at elevated temperatures. While the data in FIG. 8 suggest that the cfus/ml are decreasing over time, we find that this is not actually the case but rather cells are aggregating in the formulation as shown in FIGS. 9A and 9B. Accurate viability counts over time may be arrived at through the use of a dispersant in the dilution plating diluent.

The foregoing disclosure has been described in accordance with the relevant legal standards, thus the description is exemplary rather than limiting in nature. Variations and modifications to the disclosed embodiment may become apparent to those skilled in the art and do come within the scope of the disclosure. Accordingly, the scope of legal protection afforded this disclosure can only be determined by studying the following claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

We claim:

1. A shelf stable, water miscible suspension, consisting of:
   at least one microbe selected from the group consisting of *Trichoderma virens*; *Trichoderma atroviride*; *Trichoderma afroharzianum*; *Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof;
   a plant oil, wherein the plant oil is selected from the group consisting of soybean oil; canola oil; corn oil; peanut oil; rapeseed oil; sunflower oil; cottonseed oil; palm oil; coconut oil; safflower oil; sesame oil; and mixtures thereof;
   a galactomannan polysaccharide;
   a dispersing agent; and
   optionally, an amphiphilic glycerophospholipid;
   optionally, at least one metabolite derived from the at least one microbe; and
   wherein the at least one microbe in the suspension is viable and shelf stable for at least 52 weeks at a temperature of 25° C.

2. The water miscible suspension according to claim 1 wherein the at least one microbe is selected from the group consisting of *Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof.

3. The water miscible suspension according to claim 1 wherein the at least one metabolite derived from the at least one microbe is selected from the group consisting of 6-pentyl-pyrone; harzianic acid; the hydrophobic protein HYTRA 1; harzinolide; 1-octene-3-ol; and mixtures thereof.

4. The water miscible suspension according to claim 1 wherein the galactomannan polysaccharide is selected from the group consisting of fenugreek gum; guar gum; tara gum; locust bean gum; cassia gum; and mixtures thereof.

5. The water miscible suspension according to claim 1 wherein the amphiphilic glycerophospholipid is present and is a lecithin.

6. The water miscible suspension according to claim 1 wherein the dispersing agent is selected from the group consisting of a siloxane polyalkyleneoxide copolymer, an alkylphenoxypoly(ethyleneoxy)ethanol, polysorbate 80, and mixtures thereof.

7. The water miscible suspension according to claim 1 wherein the at least one microbe is present in an amount of at least $10^8$ Colony Forming Units (CFU) per milliliter of the water miscible suspension.

8. The water miscible suspension according to claim 1 wherein the suspension consists of:
   at least $10^8$ CFU per milliliter of the at least one microbe;
   70 to 97.5 weight % of the plant oil;
   2 to 17.5 weight % of the galactomannan polysaccharide;
   0.5 to 17.5 weight % of the dispersing agent; and
   optionally, 0 to 1 weight % of the amphiphilic glycerophospholipid, wherein the weight % is based on the total weight of the water miscible suspension.

9. A kit for forming a shelf stable, water miscible suspension, the kit consisting of:
   a first component consisting of plant oil and suspended in the plant oil, wherein the plant oil is selected from the group consisting of soybean oil; canola oil; corn oil; peanut oil; rapeseed oil; sunflower oil; cottonseed oil; palm oil; coconut oil; safflower oil; sesame oil; and mixtures thereof, at least one microbe selected from the group consisting of *Trichoderma virens*; *Trichoderma atroviride*; *Trichoderma afroharzianum*; *Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof and optionally, at least one metabolite derived from the at least one microbe;
   a second component consisting of galactomannan polysaccharide; glycerol; a preservative and water; and
   instructions directing a user to combine the first and second components with mixing to thereby form said shelf stable, water miscible suspension wherein the at least one microbe is viable and shelf stable for at least 52 weeks at 25° C.

10. The kit according to claim 9, wherein the at least one microbe is selected from the group consisting of *Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof.

11. The kit according to claim 9 wherein the at least one metabolite derived from the at least one microbe is selected from the group consisting of 6-pentyl-pyrone; harzianic acid; the hydrophobic protein HYTRA 1; harzinolide; 1-octene-3-ol; and mixtures thereof.

12. The kit according to claim 9 wherein the galactomannan polysaccharide is selected from the group consisting of fenugreek gum; guar gum; tara gum; locust bean gum; cassia gum; and mixtures thereof.

13. The kit according to claim 9 wherein the at least one microbe is present in an amount of at least $10^8$ Colony Forming Units (CFU) per milliliter of the water miscible suspension formed from the combination of the first and second components.

14. The kit according to claim 9 wherein:
   the first component consists of 80 to 99.6 weight % of the plant oil, and from 2 to 20 weight % of the at least one microbe, said weight % of the at least one microbe being sufficient to provide at least $10^8$ CFU/ml of the at least one microbe in the water miscible suspension, the weight % based on the total weight of the first component;

the second component consists of from 0.3 to 10 weight % of the galactomannan polysaccharide, 10 to 30 weight % of glycerol, 0.1 to 2 weight % of the preservative, and 60 to 90 weight % water; and wherein the instructions state the first component is to be mixed with the second component in a volume:volume ratio of from 1:4 to 4:1.

15. A shelf stable, water miscible suspension, consisting of:
a plant oil, wherein the plant oil is selected from the group consisting of soybean oil; canola oil; corn oil; peanut oil; rapeseed oil; sunflower oil; cottonseed oil; palm oil; coconut oil; safflower oil; sesame oil; and mixtures thereof, having suspended therein at least one microbe selected from the group consisting of *Trichoderma virens; Trichoderma atroviride; Trichoderma afroharzianum; Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof, wherein the at least one microbe is present in an amount of at least $10^8$ CFU/ml of the water miscible suspension;

water, a preservative, a galactomannan polysaccharide; and optionally, one or more components selected from the group consisting of at least one metabolite derived from the at least one microbe, a cyclodextrin, glycerol, humic acid, yeast extract, nitrogen, and mixtures thereof, and wherein the at least one microbe in the water miscible suspension is shelf stable for at least 52 weeks at a temperature of 25° C.

16. The water miscible suspension according to claim 15 wherein the at least one microbe is selected from the group consisting of *Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof.

17. The water miscible suspension according to claim 15 wherein the at least one metabolite derived from the at least one microbe is selected from the group consisting of 6-pentyl-pyrone; harzianic acid; the hydrophobic protein HYTRA 1; harzinolide; 1-octene-3-ol; and mixtures thereof.

18. The water miscible suspension according to claim 15 wherein the galactomannan polysaccharide is present in an amount of up to 5 weight % and is selected from the group consisting of fenugreek gum; guar gum; tara gum; locust bean gum; cassia gum; and mixtures thereof.

19. The water miscible suspension according to claim 15 wherein the glycerol is present in an amount of up to 5 weight %.

20. The water miscible suspension according to claim 15 wherein the cyclodextrin is present in an amount of up to 10 weight %.

21. The water miscible suspension according to claim 15 wherein the humic acid is present in an amount of up to 5 weight %.

22. The water miscible suspension according to claim 15 wherein the yeast extract is present in an amount of up to 5 weight %.

23. The water miscible suspension according to claim 15 wherein the nitrogen is present in an amount of up to 5 weight %.

24. A shelf stable, water miscible suspension, consisting of:
a plant oil, wherein the plant oil is selected from the group consisting of soybean oil; canola oil; corn oil; peanut oil; rapeseed oil; sunflower oil; cottonseed oil; palm oil; coconut oil; safflower oil; sesame oil; and mixtures thereof, having therein at least one microbe selected from the group consisting of *Trichoderma virens; Trichoderma atroviride; Trichoderma afroharzianum; Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof, wherein the at least one microbe is present in an amount of at least $10^8$ CFU/ml of the water miscible suspension;

glycerol, a dispersing agent;

optionally, a galactomannan polysaccharide, at least one metabolite derived from the at least one microbe; and wherein the at least one microbe in the water miscible suspension is shelf stable for at least 52 weeks at a temperature of 25° C.

25. The water miscible suspension according to claim 24 wherein the at least one microbe is selected from the group consisting of *Trichoderma virens* strain K1; *Trichoderma afroharzianum* strain K2; *Trichoderma afroharzianum* strain K3; *Trichoderma atroviride* strain K4; *Trichoderma atroviride* strain K5; and mixtures thereof.

26. The water miscible suspension according to claim 24 wherein the at least one metabolite derived from the at least one microbe is selected from the group consisting of 6-pentyl-pyrone; harzianic acid; the hydrophobic protein HYTRA 1; harzinolide; 1-octene-3-ol; and mixtures thereof.

27. The water miscible suspension according to claim 24 wherein the galactomannan polysaccharide is present in an amount of up to 1 weight % and is selected from the group consisting of fenugreek gum; guar gum; tara gum; locust bean gum; cassia gum; and mixtures thereof.

28. The water miscible suspension according to claim 24 wherein the glycerol is present in an amount of from 66 to 89 weight %.

29. The water miscible suspension according to claim 24 wherein the dispersing agent is present in an amount of from 1 to 3 weight %.

30. The water miscible suspension according to claim 24 wherein the dispersing agent is selected from the group consisting of siloxane polyalkyleneoxide copolymer, polysorbate 80, an alkylphenoxypoly(ethyleneoxy)ethanol, and mixtures thereof.

31. The water miscible suspension according to claim 24 wherein the suspension is provided in the form of a two component kit wherein,
a first component consists of the plant oil having therein at least one microbe, wherein the at least one microbe is present in an amount of at least $10^8$ CFU/ml of the water miscible suspension, and optionally, at least one metabolite derived from the at least one microbe; and
a second component consists of the glycerol, the dispersing agent, and optionally, the galactomannan polysaccharide.

* * * * *